United States Patent [19]

Helmo

[11] Patent Number: 5,700,370
[45] Date of Patent: Dec. 23, 1997

[54] BIOLOGICAL TREATMENT PLANT CONTROLLED BY FLUORESCENCE SENSORS

[75] Inventor: Kim Helmo, Karlslunde, Denmark

[73] Assignee: BioBalance A/S, Brondby, Denmark

[21] Appl. No.: 532,849

[22] Filed: Sep. 22, 1995

Related U.S. Application Data

[63] Continuation of Ser. No. 299,543, Sep. 1, 1994, Pat. No. 5,506,096, which is a continuation of Ser. No. 63,356, May 18, 1993, abandoned, which is a continuation of Ser. No. 461,088, Jan. 4, 1990, abandoned.

[30] Foreign Application Priority Data

Feb. 28, 1989 [DK] Denmark ............... 0969/89

[51] Int. Cl.$^6$ ............... B01D 17/12; C02F 3/00
[52] U.S. Cl. ............... 210/94; 210/96.1; 210/143; 422/62; 422/82.08
[58] Field of Search ............... 210/94, 143, 610, 210/611, 614, 631, 632, 745, 85, 96.1; 436/172; 422/62, 82.05, 82.08; 435/3, 29, 30; 250/461.2

[56] References Cited

U.S. PATENT DOCUMENTS

| | | | |
|---|---|---|---|
| 3,926,737 | 12/1975 | Wilson et al. | |
| 4,112,741 | 9/1978 | Kerfoot et al. | |
| 4,260,490 | 4/1981 | Moss et al. | |
| 4,385,113 | 5/1983 | Chapelle et al. | |
| 4,554,077 | 11/1985 | Brown et al. | |
| 4,564,444 | 1/1986 | Hiraoka et al. | |
| 4,577,110 | 3/1986 | MacBride et al. | |
| 4,684,469 | 8/1987 | Pedersen | 210/632 |
| 4,686,372 | 8/1987 | Satoru | 250/461.2 |
| 4,783,265 | 11/1988 | Timmons | 210/667 |
| 4,793,930 | 12/1988 | Soeder | 210/614 |
| 5,173,187 | 12/1992 | Nader et al. | 210/614 |

FOREIGN PATENT DOCUMENTS

| | | | |
|---|---|---|---|
| 0 171 158 | 2/1986 | European Pat. Off. | |
| 0 244 148 | 11/1987 | European Pat. Off. | |
| 336281 | 10/1989 | European Pat. Off. | 210/614 |
| 0 336 281 | 11/1989 | European Pat. Off. | |
| 60-220199 | 11/1985 | Japan | 210/614 |
| 62-175195 | 7/1987 | Japan | |
| WO 88/00978 | 2/1988 | WIPO | |

OTHER PUBLICATIONS

Zabriskie, Dane W., "Use of Culture Fluorescence for Monitoring of Fermentation Systems", *Biotechnology and Bioengeineering*, No. 9, 117–124, undated.

Bari, Abdul et al., "Measurement of Wastewater Treatment Efficiency by Fluorescence and UV Absorbance", 10 Apr. 1984.

Noack, Udo, "Algae Monitor Water Quality", Umwelt (1988), (11–12), 560–1, 563 (abstract).

Zabriski, D.W., et al., "Estimation of Fermentation Biomass Concentration by Measuring Culture Fluorescence", *Applied Environmental Bicrobiology*, vol. 35, No. 2, pp. 337–343 (1978)

(List continued on next page.)

*Primary Examiner*—Joseph W. Drodge
*Attorney, Agent, or Firm*—Merchant, Gould, Smith, Edell, Welter & Schmidt, P.A.

[57] ABSTRACT

A waste water purification plant for biological treatment, and optionally mechanical and/or chemical treatment, of biodegradable material present in an aqueous environment is provided. The plant in a biological treatment part contains at least one sensor which measures fluorescent emission and/or variation therein of at least one characteristic biogenic fluorophore present in the biological treatment part which comprises a mixed culture of microorganisms, and which plant further includes a data processing device connected to the at least one sensor and a control device connected to the data processing device. The plant also contains a portion for determining quality and/or quantity of the material to be treated including an additional mixed culture of microorganisms, a sample of the biodegradable material and a further sensor or sensors for measuring fluorescent emission.

6 Claims, 9 Drawing Sheets

OTHER PUBLICATIONS

Harrison, D.E.F., et al., "Fluorimetric Technique for Monitoring Changes in the Level of Reduced Nicotinamide Nucleotides in Continous Cultures of Microorganisms", *Applied Microbiology*, pp. 446–450 (Mar. 1970).

International Search Report for Danish Application No. 969/89, undated.

International Search Report for PCT/DK 90/00059, undated. Lengd Avia Instrm; Derwent's Abstract No. 12437C/07, SU–666–201; "Water microbial contamination quantitative determination from intensity of fluroescence . . . " (1977).

Vodokanal Aeration; Derwent's Abstract No. 58251K/24, SU–947–080; "Activated sludge conc. control unit by incosuing luminescence . . . " (1980).

Szwerinski et al., Chem. Abstracts citation 102:154225p (1985). Abstract of *Appl. Microbiol. Biotechnol.*, 21(1–2), 125–128 (1985).

Gorki Epidemiology; Derwent's Abstract No. 88–117714/17, SU–1339–130–A; "Measuring respiratory activity in microorganisms", (1985).

Cloete et al.,; Chem. Abstracts citation 109:215373d (1888). Abstract of *Water Res.*, 22('8), 961–969 (1988).

FLOW-SHEET

AERATION-TANK 4

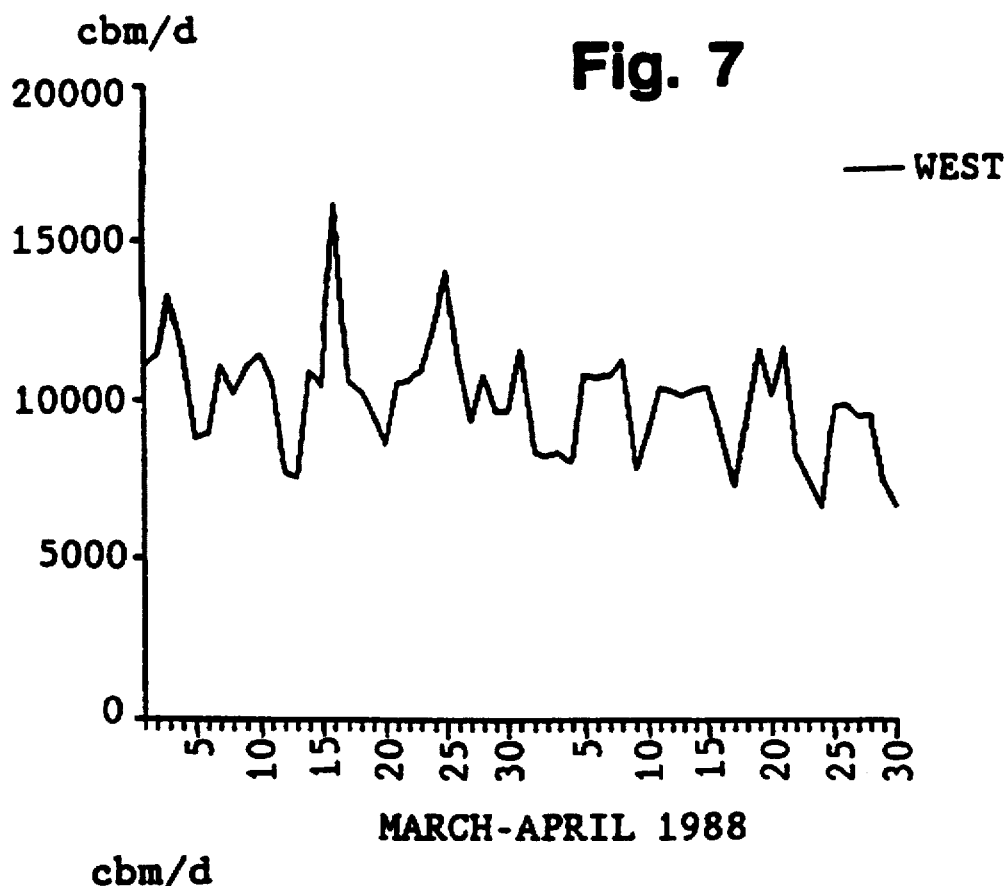
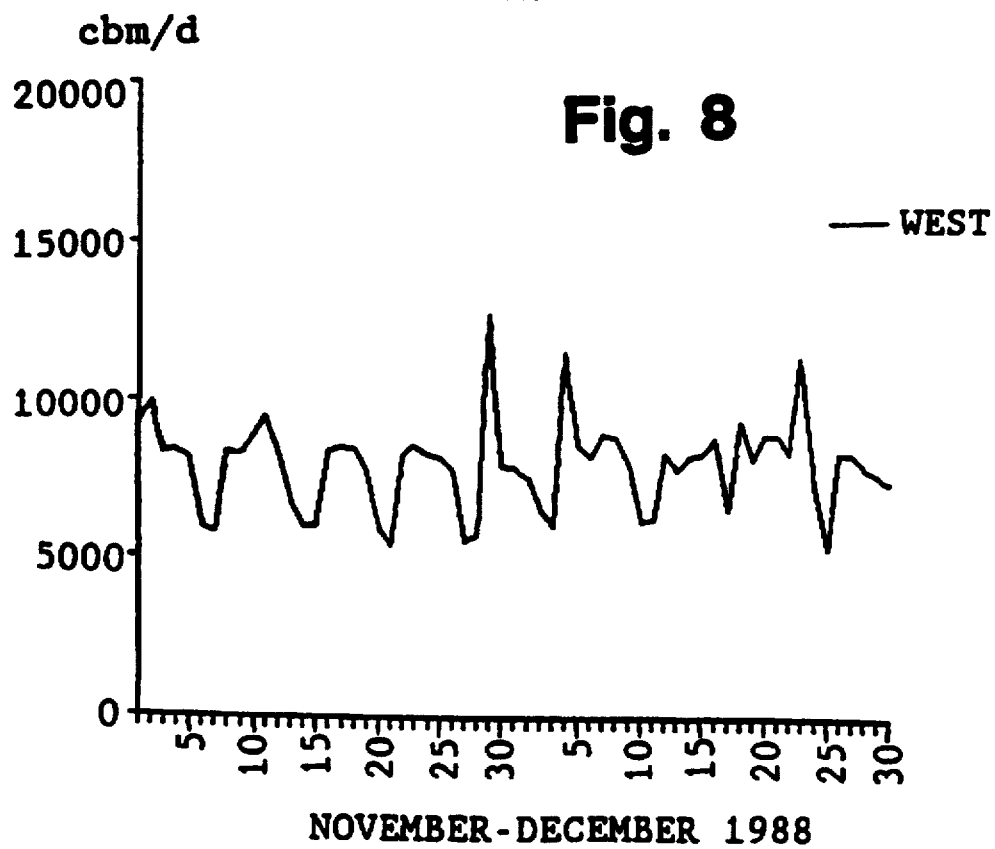

BIOLOGICAL TREATMENT PLANT CONTROLLED BY FLUORESCENCE SENSORS

This is a continuation of application Ser. No. 08/299,543, filed Sep. 1, 1994, now U.S. Pat. No. 5,500,906, which is a continuation of application Ser. No. 08/063,356, filed May 18, 1993, now abandoned, which is a continuation of application Ser. No. 07/461,088, filed Jan. 4, 1990, now abandoned which applications are incorporated herein by reference.

FIELD OF THE INVENTION

The present invention relates to a novel method for controlling and/or optimising a process wherein an aqueous biological system is treated in order to provide purified water having a substantially lower content of biodegradable material than said biological system.

TECHNICAL BACKGROUND OF THE INVENTION

Today, protection of the environment is of great concern to mankind. An ever increasing population as well as a general demand for increased quality of life expressed as a healthy and beautiful environment and at the same time a lift style based on the use of advanced technology has accentuated the need for water, especially pure water throughout the world, but especially in the industrialized parts of the world.

In highly industrialized countries, especially countries with large urban concentrations, it is necessary to treat the waste water from households and industrial production so as to avoid an unacceptable level of polluted and polluting material in the environment, i.e. in the recipients for the waste water such as lakes, rivers and other waterways, the sea, etc. The polluted and polluting material comprises a variety of substances, for example organic and inorganic substances which may or may not be decomposable in nature. Among the polluting material usually present in waste water effluents decomposable organic matter and heavy metals are of the greatest concern.

An increasing amount of the waste water, which is produced worldwide, is not subjected to some kind of treatment, such treatment being of mechanical, chemical or biological nature or any combination thereof. Generally, it is expected that there will be focused even more on waste water treatment in the future as the public awareness of environmental hazards is becoming even stronger than today.

The main purpose of purifying municipal and industrial waste water is to reduce the content of biodegradable material in the waste water, i.e. to secure that the treated waste water does not contain such amounts of biodegradable material, i.e. degradable organic and/or inorganic matter, that these amounts will lead to an unacceptable low level of oxygen in the recipient due to the amount of oxygen required for aerobic decomposition of degradable (organic) material.

In order to fulfil this purpose, it is most desirable to be able to control the various steps of the purification process. As mentioned above, these steps are typically mechanical and/or chemical and/or biological, the use of biological treatment steps in a waste water purification process usually being the most sensible part of the overall process. Today, many waste water treatment plants, especially such plants comprising biological treatment steps, use some kind of process control. Generally, process control of industrial processes is based on knowledge of one or more of the most important parameters of the process in question, such knowledge being available on-line as a measured variable of the process, the controlled variable(s) being regulated based on this on-line information about the values of the measured variable(s).

As outlined above, the most important parameter in the treatment of municipal and industrial waste water is the content, i.e. the amount and the quality, of biodegradable material. In the field of waste water treatment this parameter is conventionally measured in terms of Biochemical Oxygen Demand (BOD). BOD is a measure of the amount of oxygen required for aerobic decomposition of organic matters. Biochemical Oxygen Demand evaluates the oxygen demand of the microorganisms performing the decomposition. However, it is disadvantageous that it is necessary to perform the BOD analysis on a sample under laboratory conditions and, furthermore, the BOD analysis does not give any precise information about the potential energy available as the microbiological degradation of the biodegradable material proceeds.

Thus, the state of the art is that the actual value of the most important parameter of a waste water purification process can neither be determined or monitored on-line nor be used as a measured variable in the process control system. Up till now, the various kinds of process control in the field of waste water purification have been based on measurements of parameters such as volumes, flow rates (residence time), pH, content of oxygen and/or of suspended solids in the waste water and the like. Especially purification processes comprising a biological step are extremely difficult to operate on the basis of the information about the state of the process which is available at present since the mixed cultures of microorganisms responsible for the decomposition of organic and/or inorganic matter, i.e. the biodegradable material present in the waste water, are most vulnerable to variations in the biodegradable material loading of the step. As a result thereof, the operation of such waste water purification plants are almost solely based on empirical knowledge of the chemical and/or biological processes which are actually taking place in the various process steps.

Also, it is a disadvantage of utmost importance that it is impossible to obtain on-line information about the quality of the final effluent from a waste water purification plant, i.e. the actual content of for example biodegradable material in the effluent which is lead to environmental recipients is unknown.

OBJECT OF THE INVENTION

Therefore, it is an object of the present invention to provide a method for on-line monitoring of the microbiological activity in aqueous biological systems and optionally controlling one or several process parameters of a process wherein said aqueous biological system is subjected to mechanical and/or chemical and/or biological treatment so as to obtain as a final product purified water as well as to prevent overloading of the microbiological capacity of the biological treatment step.

It is essential that the method comprises a measurement having short response times so that the measurement is made on-line or in real time with respect to the actual processes in said system; that the method can be carried out in situ so as to avoid any of the usual disadvantages connected with sampling; and that the method is suitable for use under a variety of conditions, especially regarding temperature, pH, salinity, turbidity and other parameters which may vary depending on the particular aqueous biological system in question. Also, it is most desirable that the method has a high degree of stability and that the equipment used in the method can be operated continuously for long periods without any need for maintenance.

Another object of the invention is to provide a method for quantitatively and/or qualitatively assessing the content of biodegradable material in an aqueous biological system so as to monitor for example waste water effluents, final effluents from waste water treatment plants, recipients of the environment and the like.

BRIEF DESCRIPTION OF THE INVENTION

The present invention concerns a novel method for controlling and/or optimising a process in which a biological system comprising mixed cultures of microorganisms, biodegradable material, and optionally other soluble and/or insoluble and/or suspended substances in an aqueous environment is subjected to one or several separation processes and/or to chemical reactions and/or to biological treatment so as to obtain as a final product purified water which has a substantially lower content of biodegradable matter than said biological system, which method comprises monitoring the microbiological activity of said biological system and/or fluctuations thereof by on-line measurement of fluorescent emission and/or variations therein for at least one characteristic biogenic fluorophore present in the mixed culture of microorganisms in the system when irradiated with light and controlling one or several parameters of said process by using results from said measurement as measured variable(s) in an on-line automatisation system.

The invention is based on the discovery that it is possible to obtain a relevant assessment of the content of biodegradable material in a complex biological system as outlined above by monitoring the microbiological activity of the system and/or fluctuations thereof by on-line measurement of fluorescent emission and/or variations thereof as explained above. In another aspect based upon the same discovery, the invention relates to a method for quantitatively and/or qualitatively assessing the content of biodegradable material in an aqueous system present in the environment, for example sea water, lake water, river water or other natural or artificial waters, or in waste water which is to be subjected to mechanical and/or chemical and/or biological treatment, preferably chemical and/or biological treatment, especially biological treatment, so as to obtain as a final product purified water having a substantially lower content of biodegradable material than the waste water, the method comprising measuring fluorescent emission of one or more biogenic fluorophores present in the aqueous system and being capable of acting as indicator(s) of the level of microbiological activity and thereby of the amount of biodegradable material present in the aqueous system when irradiated with light emitted at a wavelength preferably longer than 250 nm. Preferably, examples of the biogenic fluorophores are tryptophan- and tyrosine-containing proteins, tryptophan- and tyrosine-containing peptides, tryptophan- and tyrosine-containing derivatives of amino acids, purines, pyrimidines, nucleosides, nucleotides, nucleic acids, steroids and vitamins. When irradiated with light emitted at a wavelength preferably longer than 250 nm, especially in the range of 250 nm–780 nm, the fluorescence emission of the biogenic fluorophore(s) is preferably detected at wavelengths longer than 250 nm, for example in the range of 250 nm–800 nm, and using the measured values of said fluorescence emission as basis for the assessment.

In the following description, the term "the method of the invention" designates the controlling and/or optimising method unless otherwise indicated.

By using the method of the invention, it is possible to control a process such as a waste water purification process comprising mechanical and/or chemical and/or biological treatment steps so as to eliminate overloading of the biological treatment steps with biodegradable material which overloading frequently occurs in most plants, thus providing a relatively constant effectivity of the biological treatment step(s), i.e. optimum or near optimum conditions for the mixed cultures of microorganisms and optionally other organisms which are present in the waste water subjected to biological purification and which organisms are capable of decomposing organic and/or inorganic matter.

Optimum or near optimum conditions can for example be provided by a controlled biodegradable material loading of the biological step and/or recycling rate of activated sludge to the biological treatment step so as to create an optimum or near optimum ratio between microbiological activity and biodegradable material loading.

A controlled biodegradable material loading of the biological step can for example be provided by a controlled chemical precipitation (settlement) of biodegradable material, especially biodegradable material in the form of colloid particles, in a chemical treatment step prior to the biological treatment steps. Such process control of the mentioned chemical treatment step is based on on-line information about the microbiological activity in the biological treatment steps.

Also, a controlled biodegradable material loading of the biological treatment step can be provided based on a qualitative assessment, preferably an on-line assessment, of the biodegradability of the aqueous biological system i.e. the waste water, to be processed together with on-line information about the microbiological activity in the biological treatment steps, and relevant process parameters are adjusted according to the obtained information. Among the various process parameters that are useful in this context can be mentioned the total amount of sludge in the system, rate of recycling of mechanically and/or chemically and/or biologically treated waste water (in order to lower the concentration of biodegradable material, especially of not readily biodegradable material, in the volume led to the biological treatment step), rate of recycling of untreated waste water (from storage tanks or basins), flow rate of inlet waste water led to storage tanks for later treatment, dosage rate of chemical precipitation chemicals, residence time and addition of agents capable of enhancing decomposition of not readily biodegradable material.

Thus, by use of the method the invention, it is possible to reduce or eliminate the major fluctuations/variations in the biodegradable material loading of a biological treatment step of a waste water purification plant.

Most waste water purification plants comprise at least a chemical and a biological treatment step. When used in connection with such plants, the method of the invention may result in the attainment of one or several of the following advantages:

Total requirement for oxygen is decreased,
the capacity of the biological treatment step (i.e. the volume of the aeration tanks) can be decreased,
higher degree of utilization of total capacity,
better basis for design of the purification process,
better control of the process, and
a more efficient purification process which can be expressed in terms of a higher quality of the final effluent water.

As for the biological treatment steps, advantages which may be obtained with the method of the invention, are for example:

A more stable microbiological composition, better utilization of the mixed cultures of microorganisms (biomass), better flocculation properties, and a better settlement in secondary settlement steps.

Thus, economical advantages may be obtained by using the method of the invention. Furthermore, by using the method of the invention, a more profound knowledge of the microbiological processes, i.e. the microbiological conversion, which are taking place in the biodegrading step of a waste water purification plant, may be obtained.

The use of fluorescent emission measurements of biological processes is mentioned in U.S. Pat. No. 4,686,372 and U.S. Pat. No. 4,577,110. However, none of these patents mentions the use of fluorescent emission measurements for controlling microbiological decomposition of biodegradable material or for assessing the content of biodegradable material in an aqueous system.

DESCRIPTION OF THE DRAWING

The drawing consists of 12 figures among which

FIG. 7 shows the inlet flow of industrial waste water from the separate inlet stream denoted "west" of The Central Purification Plant, the city of Holstebro, Denmark, during March and April, 1988.

FIG. 8 shows the inlet flow of industrial waste water from the separate inlet stream denoted "west" of The Central Purification Plant, the city of Holstebro, Denmark, during November and December, 1988.

Figure 1:
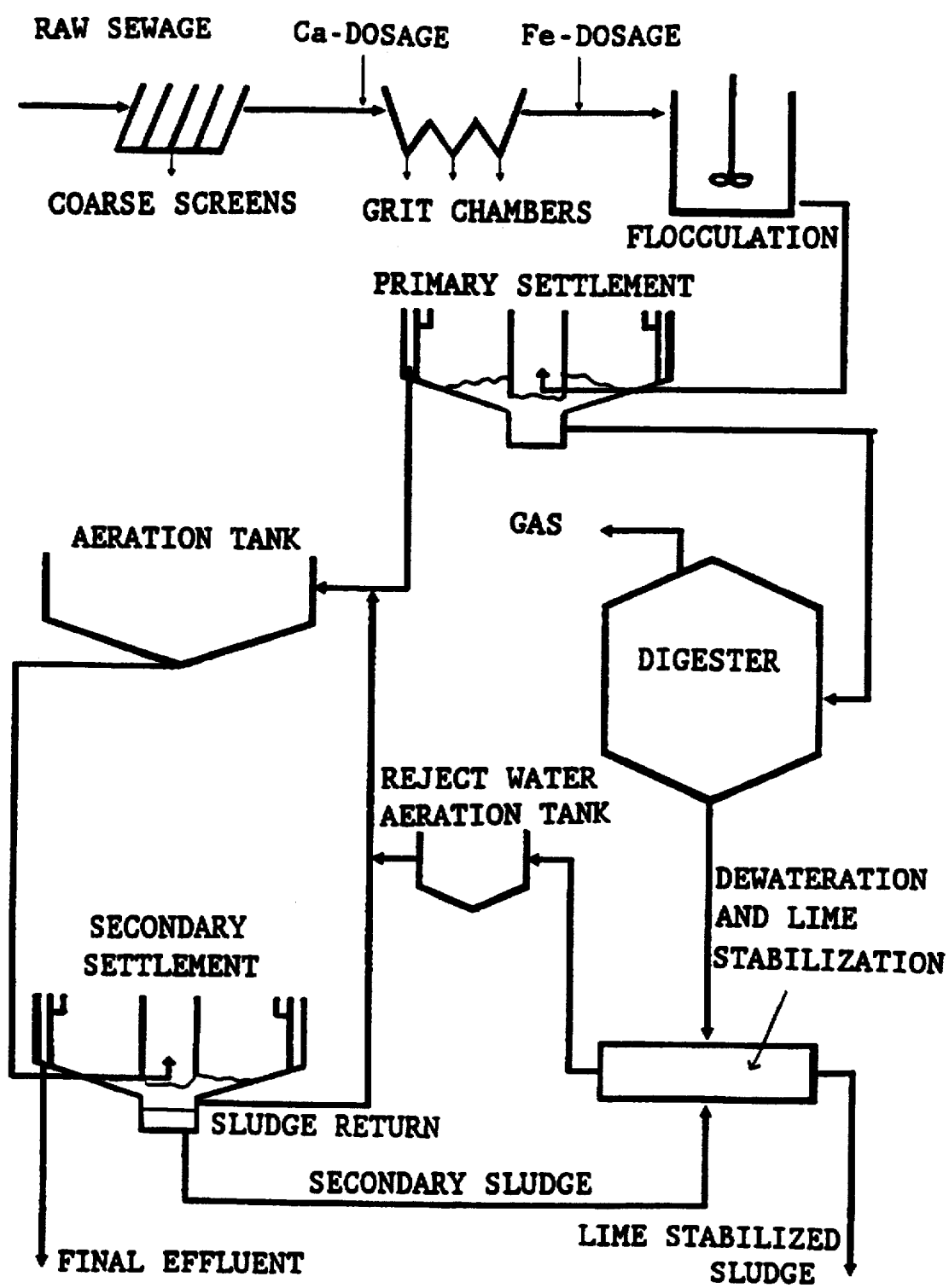
FIG. 1 shows a flow sheet of the waste water purification plant (The Central Purification Plant, the city of Holstebro, Denmark) in which the practical experiments of Example 1, 2 and 3 were carried out.

The figures are further described in the following examples.

DETAILED DESCRIPTION OF THE INVENTION

As used herein, the term "controlling" denotes the act of regulating or deliberately influencing one or more variables of a process on the basis of measurements of one or more of the variables of the process. The latter variable(s) is/are denoted measured variable(s) whereas the first mentioned variable(s) is/are conventionally denoted (a) controlled variable(s). The desired numerical value of the controlled variable is referred to as the set point, whereas a change in any variable which may cause the controlled variable of the process to change is referred to as the load. A process control system used for controlling a process such as the present is conveniently a feed-back system wherein the measured value of the controlled variable is returned to a device called the comparator wherein the controlled variable is compared with the set point. If there is any difference between the measured variable and the set point, an error is generated. This error enters a controller which in turn adjusts the final control element, for example a control valve or a pump speed regulator, in order to return the controlled variable to the set point.

The term "mixed cultures of microorganisms" as used herein refers to cultures comprising a plurality, normally a wise variety, of species of microorganisms such as autotrophic as well as heterotrophic and aerobic, anaerobic or facultative bacteria, as well as lower eucaryotic organisms such as protozoa; yeasts; fungi, and other organisms usually present in activated sludge in the biological treatment step of a waste water purification plant, for example multicellular organisms such as slipper animalcule (Paramecium) and parasites, especially bacteria-consuming parasites. Such mixed cultures of microorganisms as defined above may also be denoted biomass or activated sludge. The term "activated sludge" is conventionally used for mixed cultures of microorganisms as defined above which are present in the biological treatment step in order to degrade the biodegradable material, i.e. especially decomposable organic and/or inorganic matter. Such mixed cultures of microorganisms utilize the nutrition in the waste water to be treated and thereby convert organic and inorganic matter to biomass and to end products of metabolism such as nitrates, nitrogen, sulphates, phosphates, carbon dioxide etc. This conversion can take place under anaerobic, aerobic or anoxic conditions. The actual composition of the mixed cultures of microorganisms may vary widely since the composition is highly dependent on the prevailing conditions.

As used herein, the term "biodegradable material" refers to organic and/or inorganic matter which is biologically decomposable, such decomposition taking place by subjecting the organic and/or inorganic matter, especially the organic matter, to a transformation process conducted by mixed cultures of microorganisms (biomass, activated sludge), the transformation process taking place in an aqueous environment, for example water, waste water, sewage, lake water, sea water, river water and the like. The mixed culture of microorganisms uses the present biodegradable material as a source of nutrition and/or energy, thus converting the biodegradable material to additional biomass to end products of metabolism such as nitrates, nitrogen, sulphates, phosphates, carbon dioxide etc.

The term "fluorescence" or the term "fluorescent emission" refers to the emission of radiant energy by a molecule or ion in the excited state. The molecule or ion reaches the excited state by absorption of radiant energy. Absorption of (or excitation by) ultra-violet or visible radiation causes an electronic transition (in $10^{-18}$ sec.) so that the molecule is excited from the electronic ground state to some vibrational sublevel of the first electronic excited state. This absorption of light is usually referred to as excitation. After excitation, the molecule must emit a quantity of energy equivalent to that absorbed if it is to return to the electronic ground state. This energy can take several forms, for example light, heat, etc. When said quantity of energy is emitted as light having longer wavelengths (lower energy) than the wavelengths of the light used for excitation and the time scale for this emission of light is approximately $10^{-8}$ sec., then such emission is denoted fluorescence.

As used herein, the term "biogenic fluorophores" denotes substances synthesized by living material (living cells), the molecules of such substances being capable of fluorescing when irradiated with light. Biogenic (biological) fluorophores include proteins, especially tryptophan- and tyrosine-containing proteins, tryptophan- and tyrosine-containing peptides, tryptophan- and tyrosine-containing derivatives of amino acids, co-factors, purines, pyrimidines, nucleosides, nucleotides, nucleic acids, steroids, vitamins and others. In this context, NADH (nicotineamide adenine dinucleotide) and NAD(P)H are preferred examples of biogenic fluorophores. Other examples of biological substances capable of fluorescing are tyrosine, tryptophan, ATP (adenosine triphosphate), ADP (adenosine diphosphate), adenine, adenosine, estrogens, histamine, vitamin A, phenylalanine, p-aminobenzoic acid, dopamine (3,4-dihydroxyphenylethylamine), serotonin (5-hydroxytryptamine), dopa (3,4-dihydroxyphenylalanine), kynurenine and vitamin B12.

Each biochemical or chemical molecule (biogenic fluorophore) has a characteristic excitation and fluorescence spectrum. Usually, the fluorescence spectrum or fluorescence band is split into two or more peaks or maxima, each peak occurring at a specific wavelength. To detect the fluorescence emission of a fluorescing molecule, it is a necessity to detect this emission at a wavelength which is within the envelope of the fluorescence band for the fluorophore, preferable at a wavelength corresponding to a peak in the fluorescence spectrum. Also, the fluorophore should be irradiated with light emitted at a wavelength which is within the envelope of the excitation band for the fluorophore, preferably at a wavelength corresponding to a peak in the excitation band.

The term "characteristic" as used in connection with biogenic fluorophore(s) denotes that the biogenic fluorophore is one which is inherently produced by the living biological material in question, i.e. the mixed culture of microorganisms, in an amount reflecting the biological activity, for example the metabolic activity, of the living material. Typically, the biogenic fluorophores are present as intracellular substances in the microorganisms.

The excitation peak and fluorescence peak, respectively, of important examples of the above-mentioned fluorophores appear from the table below:

TABLE I

Examples of Biologically Important Fluorescent Substances

| | Excitation Peak (nm) | Fluorescence Peak (nm) |
|---|---|---|
| * tyrosine | 275 | 303 |
| 3,4-dihydroxyphenylalanine (Dopa) | 345 | 410 |
| * tryptophan | 287 | 348 |
| kynurenine | 370 | 490 |
| 5-hydroxytryptamine (serotonin) | 295 | 330 |
| phenylalanine | 260 | 282 |
| 3,4-dihydroxyphenylethylamine (dopamine) | 345 | 410 |
| histamine | 340 | 480 |
| vitamin A | 372 | 510 |
| flavins | 450 | 535 |
| NADH & NAD(P)H | 340 | 460 |
| p-aminobenzoic acid | 294 | 345 |
| vitamin B12 | 275 | 305 |
| estrogens | 285 | 325 |
| ATP, ADP, adenine, adenosine | 272 | 380 |

* Responsible for protein fluorescence

It is preferred that in the practical use of the method of the invention, the light is emitted at a wavelength longer than 250 nm, especially 250 nm–780 nm, for example about 340 nm, and fluorescence emission is detected at wavelengths longer than 250 nm, preferably 250 nm–800 nm, especially 280–500 nm, for example about 460 nm.

The term "aqueous environment" as used herein refers to a liquid containing water as the basic predominant constituent, preferably more than 80% by weight, more preferably more than 90% by weight, especially more than 95% by weight, for example more than 97% by weight, most preferably more than 99% by weight, or water, the liquid acting as solvent and/or dispersing medium, the liquid comprising soluble and/or insoluble and/or suspended and/or dispersed substances, material and/or mixed cultures of microorganisms as defined above, thus creating a biological system.

As used herein, the term "waste water" is used as a common designation for aqueous effluents containing organic and/or inorganic substances which are present or formed in an environment as a consequence of the presence and/or activity of human beings, including industrial activity in its widest sense which e.g. comprises domestic and industrial activity, agriculture, forestry and fishing industry and which it is desired to treat so as to obtain purified water with the main purpose of maintaining and/or improving the environment and/or to provide a production of purified water which can be re-used as tap water. Typically, waste water is produced constantly or seasonally.

As used herein, the term "separation processes" refers to processes wherein material and/or substances are separated from each other, especially such processes wherein the material and/or substances to be separated are present in different physical states, i.e. in liquid and solid phase, respectively, or gaseous and solid phase, respectively, or gaseous and liquid phase, respectively, but also to processes separating two liquid phases. Preferred separation processes are such processes conventionally being used in water or waste water purification processes and mainly being of mechanical nature, such as removal of visible polluting materials (solids) from the incoming waste water to a waste water purification plant, flotation and sedimentation, for example by using equipment such as coarse screens, fine screens, comminutors, scimming tanks, grit chambers, settling tanks, and sedimentation tanks.

As used herein, the term "chemical reactions" refers to chemical reactions having biodegradable material as defined above as one of the reactants, the other reactant(s) being for example precipitation chemicals capable of reacting with biodegradable material so as to form (a) precipitate(s) which may settle from the liquid. Also, the term "chemical reactions" comprises the process of flocculation, especially the flocculation of colloidal solids and very finely defined suspended matter which are rendered settleable by the addition of coagulants. These are chemicals dispersing in water as fine particles loaded with positive electric charge neutralizing the electric field of the natural solid particles in colloidal suspension. as a result of this phenomenon, the colloidal suspensions crowd together to form flocks which become larger and larger due to flocculation. The flocks settle, thus separating from the liquid, due to the gravitational force, at the same time catching and entraining particles not present in flocks.

As precipitation chemicals and/or coagulants can conveniently be used lime, hydrated lime and salts of di- or trivalent metals such as ferric chloride, ferric sulphates, ferrous sulphate, aluminum sulphate, sodium aluminate, aluminum chloride, magnesium carbonate hydroxide, calcium carbonate, calcium hydroxide, activated silicates, guar gums, starches, tannins, sodium alginate, polyaluminium sulphate, polyaluminium hydroxychloride, Bio-Flock®, and synthetic polyelectrolytes, for example Zetag®, Magnafloc, Superfloc®, etc.

In the following, the process of chemical precipitation of biodegradable material and the process of flocculation and sedimentation is commonly referred to as chemical precipitation. Also, precipitation chemicals and coagulants used for these processes are commonly referred to as precipitation chemicals.

In order to provide optimum or near optimum conditions for the chemical precipitation process, the pH of the biological system subjected to chemical reactions should be kept within the range of about 6.5 and about 11.0, the optimum or near optimum pH-value being dependent on the precipitation chemical used. Thus, the pH of the biological system subjected to a purification process should be continuously adjusted in order to obtain the best possible results of the chemical reaction. For example, when ferrous sulphate is used, pH is preferably in the range of 8–11. The temperature is conveniently the ambient temperature.

By the term "biological treatment" as used herein is meant a treatment of a biological system so as to substantially reduce the content of biodegradable material in the biological system by subjecting the biological system to a biodegradation process. This process involves subjecting the biological system to contact with microorganisms capable of degrading biodegradable material of the biological system. For instance, the biological system is introduced into a tank, a basin or the like containing mixed cultures of microorganisms, i.e. activated sludge (biomass), wherein the biodegradable material in the biological system to be treated is degraded by the microorganisms present.

Normally, in this biological treatment, the microorganisms flocculate and the flocculated microorganisms are brought into contact with the biological system to be treated. The distribution of the flocculated microorganisms in the biological system is obtained by means of aeration (in the cases of aerobic decomposition conditions), optionally in combination with stirring. When the microbial decomposition of the biodegradable material has terminated, the flocculated microorganisms are usually separated from the suspension, often by simply allowing the suspension to settle. Preferably, at least part of the settled material which contains substantial amount of flocculated microorganisms is recycled to the inlet of the biological treatment step, wherein it is mixed with the biological system which is to be subjected to biodegradation. Most often, it is necessary to remove part of the biomass, i.e. the microorganisms produced as a result of the decomposition, from the biological treatment step. This material is subjected for example to filtration and is deposited in any convenient manner.

Depending on the mixed cultures of microorganisms which are present in the biological treatment step, it may be necessary to adjust pH of the biological system to be treated so as to obtain optimum or near optimum decomposition conditions. Generally, it is preferred that the pH of the biological system to be treated is within the range of 6–9 as this range will be tolerated by lost microorganisms. In most cases the preferred pH-range is 7–8. If possible, also the temperature of the biological system to be treated should be adapted to the mixed cultures of microorganisms present. Most microorganisms tolerate temperatures within the range of 10°–70° C.; psychophilic microorganisms tolerate temperatures in the range of 5°–25° C., mesophilic microorganisms tolerate temperatures in the range of 25°–40° C., and termophilic microorganisms tolerate temperatures in the range of 40°–60° C. In some cases, it may be advantageous to add further nutrients to the biological system to be treated in the biological treatment step if these are deficient in certain essential or biodegradation enhancing substances. In any case, the biological system to be treated should be adapted in order to obtain optimal growth conditions, i.e. a maximum specific growth rate for the microorganisms present in the mixed cultures of microorganisms. Such optimum conditions may be determined by preliminary experiments on a pilot or laboratory scale equipment.

By the term "purified water having a substantially lower content of biodegradable matter than the biological system" is meant water which has a concentration of biodegradable matter which is at least 5 times smaller than in the biological system, preferably at least 10 times smaller, more preferably at least 20 times smaller, and most preferably at least 50 times smaller, than in the biological system. In many cases, the final product is pure water.

By the term "pure water" is meant water having a concentration of carbon-, nitrogen- and/or phosphor-containing components which are at such a low level that there is practically no such material available for further biological or microbiological growth in the purified water itself or in the recipients for the purified water. Any biological or microbiological growth in recipients of pure water is not caused by the admission of the pure water into the recipient. In terms of biological Oxygen Demand (BOD), Danish legislation has set an upper limit of 15 mg/l in the final effluent from waste water purification plants, i.e. for pure water, which can then serve as a practical numerical guideline for defining the term "pure water" herein. Regarding the content of suspended solids in purified water, it is possible to remove substantially all suspended solids from waste water by adding (an) additional separation process step(s), for example sand filter(s), to the total purification process.

By the term "microbiological activity" is means the metabolic activity of the mixed cultures of microorganisms present in the biological system and/or in the biological treatment step. In all living cells, the electron carriers NADH and NAD(P)H are present. They play a most important role in cellular metabolism: The NADH and NAD(P)H play keyroles in catabolism and anabolism, respectively. The cells maintain a pool of these reduced pyridine nucleotides for various reduction reactions. For example, in aerobic metabolism the NADH produced in the citric acid cycle donates its electrons to the respiratory chain enzymes. On the other hand, in anaerobic metabolism, the NADH produced in glycolysis donates its electrons to reducible intermediates such as acetaldehyde, butaraldehyde and ethanol. The microorganisms can be present in different metabolic states depending upon the conditions in the environment. Microorganisms which are growing aerobically are in a different metabolic state when compared to those growing under anaerobic conditions. In the former, the oxidative/phosphorylation pathway is active and the oxygen availability maintains the microorganisms in a more oxidative metabolic state when compared to microorganisms under anaerobic conditions. Thus, depending on the metabolic state, the microorganisms maintain a higher or a lower NAD(P)H pool.

Without being limited to any theory, it is believed that in case of high concentrations of biodegradable material in the aqueous biological system, the microorganisms use part of their pool of NADH, i.e. the energy pool, in degradation of the biodegradable material, thus showing a high level of activity which in turn results in a low level of NADH. At low concentrations of biodegradable material in the aqueous system, the microorganisms have the possibility of converting the energy released as a result of the degradation processes to bound (potential) energy. This bound energy can for example be present in the form of an increased amount of microorganisms or of increased concentration of energy-rich substances such as NADH in the microorganisms. It would seen to be relationships as the ones presumed here, combined with the surprising possibility of using the fluorescent measurements in the highly mixed and complex systems here contemplated which makes it possible to use the fluorescence measurement for the controlling or assessing purposes according to the invention.

Furthermore, it is contemplated that the quality of a biodegradable material or more typically fluctuations of the quality in terms of biodegradability may be evaluated by use of NADH measurements. More specifically, fluctuations in the amount of NADH measured from a microorganism culture present in a biological system also comprising the biodegradable material reflects fluctuations in the quality of the biodegradable material. Thus, the relative amounts of NADH measured from a biological system as defined above reflect the relative biodegradability of the biodegradable material present in said system.

By the term "relative amount" is meant the increase or decrease of NADH measured in a biological system comprising a mixed culture of microorganisms and a biodegradable material as a result of fluctuation in the biodegradability or quality of the biodegradable material. Alternatively, the relative amount of NADH may be evaluated by comparing the NADH measured from the biodegradable material, the biodegradability of which is to be evaluated, with the NADH measured from a biological system comprising the mixed culture of microorganisms and a material of known biodegradability. In the latter case, the biodegrading capacity of the mixed culture of microorganisms should be similar in the two NADH measurements.

In the present context, the term "biodegradability" as used with reference to the quality of a biodegradable material means the ease with which the biodegradable material is decomposed by a mixed culture of microorganisms, e.g. in a biological system as defined above, in terms of the energy demand of such decomposition. Thus, readily biodegradable materials confer a relatively low energy demand to the microorganism culture to be decomposed, whereas less readily biodegradable materials require a much higher amount of energy in order to be decomposed.

It is well known that two main systems exist for uptake of biodegradable substances by microorganisms, i.e. one system based on the principle of active transport of the substance through the cell membrane or cell wall and one system based on the principle of passive transport through the cell membrane or cell wall. It is believed that readily biodegradable materials, i.e. materials of a high biodegradability, are easily or immediately assimilated by microorganisms of the culture in question using the active as well as the passive transport system. Thus, such materials are contemplated to be capable of diffusing through the cell wall of the microorganisms of the culture without having to be modified in any substantial manner requiring energy input from the microorganisms, and subsequently be decomposed by intracellularly metabolic processes in the microorganisms. Less readily biodegradable materials are such which can not, either by passive or active transport, diffuse through the cell wall without first having been modified. It is contemplated that the less biodegradable materials are of dimensions which are not suited to pass through the cell wall or sell membrane, either because of their steric structure or because of their size. Such materials have to be modified, e.g. degraded into substances of a suitable dimension, before being able to diffuse through the cell wall or membrane and then subjected to the intracellular decomposition. The modification is presumed to comprise degradation or cleavage of the components of the biodegradable material into smaller molecules, e.g. by hydrolysis.

The critical dimension of the material which may pass the cell membrane or cell wall is different for active and passive transport, respectively. In the case of a biodegradable material mainly comprising carbon polymers which is to be uptaken by passive transport, these should preferably be cleaved into carbon compounds comprising a lower number of carbon atoms such as a carbon chain of 2 carbon atoms. It is believed that compounds containing no more than 2 carbon atoms may pass the cell wall or cell membrane without any difficulty, whereas compounds containing a carbon chain of more than 2 carbon atoms have to be modified prior to diffusion. In the case of active transport, larger molecules such as glucose may be transported through the cell wall or cell membrane without requiring too high amounts of energy.

The necessary modification of not readily biodegradable materials is contemplated to be accomplished at least partly by the microorganisms of the culture. Thus, it is believed that the microorganisms synthesize substances, e.g. hydrolytic enzymes or extracellular enzymes such as amylases, lipases or proteases, which are capable of modifying the biodegradable material in the desired manner. This synthesis requires energy, e.g. in the form of NADH. Thus, by measuring the relative amount of NADH it is possible to estimate the relative energy consumption of the microorganisms and thus evaluate fluctuations in the biodegradability of the biodegradable material.

It is contemplated that a decrease in the relative amount of NADH, e.g. as evaluated by measurement of the fluorescence emission of NADH from the microorganism culture using the principles of fluorescence emission measurements as stated herein, indicates that the biodegradable material has a reduced biodegradability, whereas an increase in the relative amount of NADH reflects an increased biodegradability. This is indicated by the results of the experiments described in Example 11 hereinafter, in which the fluorescence emission of NADH from a microorganism culture is highly increased when the microorganisms are fed on an immediate assimible carbon source (glucose) the consumption of which require a lower amount of energy compared to more complex carbon sources, vide the above theory.

In accordance with the above explanation, it is possible to evaluate the biodegradability of a given material by a method comprising measuring the amount of NADH present in a biological system comprising mixed cultures of microorganisms and the material, the biodegradability of which is to be evaluated, comparing the measured amount of NADH with the amount of NADH present in a biological system comprising a mixed culture of microorganisms having a similar biodegrading capacity and a biodegradable material of known composition, and determining the difference in the amount of NADH present in the two biological systems.

The material may be any biodegradable material, e.g. as defined above, and the method is particularly interesting in connection with materials which are to be decomposed, e.g. by use of the method of the invention.

The biodegradability of a biodegradable material fed to a waste water purification plant may be an important parameter in the control of said plant in making it possible to more precisely adapt the biodegradation processes of the plant to the biodegradability of the material to be treated and thus for instance avoid overloading of the plant, e.g. by controlling the amount of material fed to the plant or to certain steps of the process carried out in the plant or by modifying the material prior to or during the biodegradation treatment in the plant. Furthermore, the above method of evaluating biodegradability may be used in continuous analysis of the quality of waste water from various sources, e.g. the outlet from various types of industries. For instance, it is possible to determine sudden outlet of various toxic substances, e.g. heavy metals, organic solvents, surfactants and other chemical substances, which are believed to put a burden on the microorganism culture and thus lead to fluctuations in NADH value in the same manner as explained above or even to death of the microorganism culture.

As used herein, the term "on-line measurement" denotes measurements having short response times, that is the numerical value or electrical signal obtained as a result of the actual measurement is recorded substantially momentarily with respect to the process.

By the term "process parameter" is meant a physical quantity which under certain conditions is unchanging in contrast to other physical quantities which may vary, and subjected to the fact that the former physical quantity may vary itself when the certain conditions change. Thus, under certain circumstances, a process parameter is a process variable. In a given purification process, examples of unchangeable process parameters are the volume capacities of the various tanks, basins, etc., and the size and capacity of other equipment used in the process. Examples of process parameters which may be controlled during the operation of the process, i.e. process variables, are biodegradable material loading (concentration and quality), oxygen concentration, pH, temperature, turbidity, dosage rate of precipitation chemicals, dosage rate of enzymes capable of converting not readily biodegradable carbon-containing material into readily biodegradable carbon-containing material, rate of recycling of activated sludge, inlet flow rate, outlet flow rate, stirring rate, oxygen dosage rate, air dosage aeration) rate, total amount of activated sludge in the system rate of recycling of activated sludge.

Based upon knowledge about the process in question and the plant in which the process is carried out, the person skilled in the art is capable of selecting proper process parameters to be controlled based on the variations in the fluorescence emission and/or variations thereof measured on the system.

In the practical use of the method, it is often preferred to monitor the fluorescent emission of the system during an initial trial period and carefully monitoring the effect of increasing or decreasing treatment to reduce the biodegradable material, partly on the system proper and partly on the fluorescent emission, thus establishing correlation between the effect and interaction between treatment parameters, the condition of the system proper and the fluorescent emission measurement, so as to identify critical and/or suitable treatment measures which most efficiently and/or most economically can be used to control the system on the basis of the measured fluorescent emission. In practice, the fluorophors or fluorophores measured is/are selected from the group consisting of tryptophan- and tyrosine-containing proteins, tryptophen- and tyrosine-containing peptides, tryptophan- and tyrosine-containing derivatives of amino acids, purines, pyrimidines, nucleosides, nucleotides, nucleic acids, steroids and vitamins, and the measurement is suitably carried out using on-line fluorescence sensor equipment, such as, e.g., equipment of the type used in the examples.

The light with which the system is irradiated is suitably light emitted at a wavelength longer than 250 nm, and the fluorescence emission is preferably detected at a wavelength of 280–500 nm. The wavelength should of course be adapted to the particular system, in particular the kind of fluorophores present in the system.

In accordance with what is indicated above, important embodiments of the method are embodiments wherein the fluorophore is a nicotinamide adenine dinucleotide such as NADH or NADPH. In this case, the light is preferably emitted at a wavelength of about 340 nm, and said fluorescence emission is detected at a wavelength of about 460 nm.

NADH/NADPH are important elements of the metabolic pathways, and thus these substances are directly related to the capability of certain microorganisms to metabolically convert biodegradable substances to harmful, disposable substances.

When the fluorophore is NADH or NADPH, and the quality of the biodegradable material led to the biological treatment step is such that the biodegradable material is not predominantly consisting of easily assimilible substances, the control of the process is performed so that one or several of the parameters of the process is/are controlled in the direction reducing the content of biodegradable material in said system, especially the content of biodegradable material present in a part of the system subjected to biological treatment, when a reduced fluorescent emission is recorded in the biological treatment step and is controlled in the direction allowing an increased content of biodegradable material when an increased fluorescent emission is recorded in the biological treatment step.

In a particular embodiment of the method, biodegradable material present in waste water is precipitated in a chemical reaction step of a waste water treatment plant, preferably in a primary settlement tank thereof, preferably by addition of precipitating salts, and the dosage rate of said salt(s) added to the waste water is controlled on the basis of on-line measurement of fluorescent emission and/or variations therein for one or more biogenic fluorophores present in the system, when irradiated with light. In this case, the precipitating salts may suitably be selected from the group consisting of di- or trivalent metals, or more preferably iron salts, aluminium salts, sodium salts, magnesium salts and/or calcium salts or a mixture thereof, most preferably ferrous sulphate, ferric sulphate or ferric chloride.

Furthermore, it is contemplated that in order to provide a relatively constant effectivity of the biological treatment step(s), i.e. optimum or near optimum conditions for the mixed culture of organisms and optionally other organisms present in the waste water subjected to biological treatment and which organisms are capable of decomposing organic and/or inorganic matter (biodegradable material), it is advantageous to add decomposition enhancing agents when the unprocessed waste water has a high concentration of not readily biodegradable material.

As decomposition enhancing agents can be used for example waste-modifying agents such as enzymes capable of converting the not readily biodegradable material to easily assimilible substances. The enzymes can be added in the form of technical grade enzymes or as a fermentation liquid comprising the desired enzymes in an unrecovered form. A further example of decomposition enhancing agents is readily biodegradable substances which are believed to provide the mixed culture of microorganisms with the necessary amount of energy for decomposing the more heavily degradable material, since the substances are easily or immediately assimilable by the microorganisms, thus solely having the function of nourishment providing new energy during the intracellular metabolism of the microorganism.

In a preferred embodiment of the invention, industrial and municipal waste water is subjected to a waste water purification process comprising mechanical, chemical and biological treatment steps. The actual process design of such a waste water purification process, that is the actual unit operations and the equipment used, can vary widely. An example of the process design of a waste water purification plant is shown in FIG. 1. The incoming waste water may comprise one or more separate inlet streams. If the waste water purification process is designed for treating relatively large volumes, e.g. more than 20% of the total volume supplied of industrial waste water having high concentrations of biodegradable material, such industrial waste water is preferably supplied to the process (the plant) in a separate inlet stream.

Fluorescence sensor equipment capable of emitting light at a wavelength preferably longer than 250 nm, especially of about 340 nm, and detecting fluorescence emission at a wavelength of 280–500 nm, especially about 460 nm, is placed in the aeration tank of the biological treatment step. The actual placing of the fluorescence sensor equipment is not critical. However, the fluorescence sensor equipment should be protected from "false" light since sun light may interfere and influence the measurement. Thus, it may be necessary to shield the fluorescence sensor equipment so as to avoid the intrusion of "false" light into the sensor equipment. The fluorescence sensor equipment used is capable of measuring fluorescent emission of nicotinamide adenine dinucleotide (NADH). Thus, the concentration of NADH in the aeration tank is measured by means of the fluorescence sensor equipment. The concentration of NADH is a quantitative indicator of the microbiological activity in the aeration tank, and thus, the results of the fluorescent emission measurement is used as a measure for the actual state of the mixed cultures of microorganisms present, i.e. The microbiological activity. The fluorescence sensor equipment is capable of measuring the fluorescent emission of NADH in terms of Normalised Fluorescence Units (NFU) since it is calibrated in well-defined NADH solutions. One NFU corresponds to a change in fluorescence caused by 0.122 µM NADH concentration at 30° C., pH 8.0 in the concentration range of 1.0 to 25.0 µM NADH. The recorded values of NFU are proportional to the content of NADH (reduced form) in the microorganisms present in the aeration tank.

The sensor should be placed in the aeration tank in a position of thoroughly mixing and without any interference from "false" light, e.g. day light (typically 10–15 cm under the water surface is sufficient). Also, it is important that the light emitted from the sensor can be transmitted "freely" into the surrounding water. The sensor is equipped with a quarts window through which the light to and from the sensor is transmitted. By using quarts it is secured that no attachment will take place during operation, thus interfering the recordings.

Usually, NFU recordings from one sensor placed in the aeration tank is sufficient to obtain the desired information, but more than one sensor can be used if necessary, dependent of the actual design of the biological treatment step.

Prior to the biological treatment step (the aeration tank), the separate inlet of industrial waste water having a high concentration of biodegradable material is preferably subjected to a chemical reaction by addition of ferrous sulphate. The purpose of the chemical reaction is to qualitatively and/or quantitatively precipitating biodegradable material in the waste water, especially substances of pure biodegradability, for example fatty acids, especially substances in the form of colloid particles.

By chemical precipitation of a part of the biodegradable material in the waste water, the difference between the minimum loading and the maximum loading of the aeration tank with biodegradable material is reduced. This reduction of the possible variation in the biodegradable material loading the biological treatment step results in better conditions for the mixed cultures of microorganisms present and the biodegradation process is operated more steadily.

The recorded values of NFU in the seration tank is transmitted to a controller. The set point of the control system may be constant or may preferably vary according to a preset function. It is preferred to determine the preset function for each individual waste water purification process by analyzing the hourly, daily, weekly and seasonal variations in the biodegradable material loading of the purification process. Thus, the preset variations of the set point are a matter of experience, i.e. based on observed facts. For example, the set point may vary substantially as the variations in biodegradable material loading shown in FIG. 11.

The output signal from the controller adjusts the final control element, i.e. is a pump speed regulator, causing a change in the dosage rate of ferrous sulphate added to the separate stream of industrial waste water subjected to the chemical reaction.

It is contemplated that the amount of precipitation chemicals, i.e. for example ferrous sulphate, added to the waste water in a chemical reaction step in order to precipitate biodegradable and/or biological material is of the same magnitude as in the case of addition of precipitation chemicals based on the content of total phosphor (P) in the inlet waste water (raw sewage) and the final effluent (purified water). In the case of a desired phosphor concentration in the final effluent of 1–2 mg P/liter, the mole ratio of added metal ion and total phosphor in inlet waste water should be the following:

Simultaneous precipitation, Fe(II) or Al(III), mole ratio= 1–1.5

Pre-precipitation, Ca(II)+Fe(II), pH 8–9, mole ratio=1 or pre-precipitation, Al(III), mole ratio=1–2

Direct precipitation, Al(III), mole ratio=1.5

Post-precipitation, Al(III), pH 6.5–7.2, mole ratio=1–2

Corresponding to the above, when the desired phosphor concentration in the final effluent is in the range of 0.3–0.5 mg P/liter, the mole ratio of added metal ion and total phosphor in inlet waste water should be the following:

Simultaneous precipitation, Fe(II) or Al(III), mole ratio= 2+contact filtration Fe(II) or Fe(III), mole ratio=2

Post-precipitation, Al(III), pH 5.5–6.5, mole ratio=2+ contact filtration, Fe(III), mole ratio=2

Pre-precipitation, Ca(II)+Fe(II), pH 9–10, mole ratio=1.5 or Al(III), mole ratio=2

Furthermore, it is vital that the concentration of oxygen and of activated sludge (biomass) in the biological treatment step, i.e. in the aeration tanks, should be controlled in order to keep a relatively constant concentration thereof. These levels should only be allowed to fluctuate within a very narrow range, at least when short periods of time (for example hours, days) are considered. In the long run, the levels of oxygen and of activated sludge may alter to some extent without severally damaging the microbiological activity of the mixed cultures of microorganisms present in the seration tank. Since oxygen is essential for the biodegradation process, rapid and large fluctuations in the oxygen concentration are most damaging for the composition of the variety of species of microorganisms present.

In another embodiment of the invention, the C/N (carbon/nitrogen) ratio of the dinitrification step can be controlled and/or optimised based on measurements/recordings of the fluctuations of NADH or NADPH present in the mixed culture of microorganisms in a similar way as explained above for the embodiment of the invention wherein the fluorescence measurements take place in the aeration tank. In this case, the light is preferably emitted at a wavelength of about 340 nm, and the fluorescence emission is detected at a wavelength of about 460 nm.

The C/N ratio is a critical parameter in the denitrification process, since the ratio should not be below a given value which can be empirically determined for any actual denitrification process step of a waste water purification plant. If such a shortage of readily biodegradable carbon-containing material (corresponding to "C" in the C/N ratio) exists in the denitrification process, the recorded NFU is relatively low or decreasing. On the basis of the information gained by the fluorescence measurement, the C/N ratio can be controlled by proper adjustment of relevant process parameters as mentioned above.

In another embodiment, the present invention relates to a method of quantitatively and/or qualitatively assessing the content of biodegradable material in an aqueous system or fluctuations in said content, the method comprising measuring fluorescent emission of one or several characteristic biogenic fluorophores capable of acting as indicator(s) of the level of microbiological activity and thereby of the amount and/or quality of biodegradable material present in the aqueous system, preferably tryptophan- and tyrosine-containing proteins, tryptophan- and tyrosine-containing peptides, tryptophan- and tyrosine-containing derivatives of amino acids, purines, pyrimidines, nucleosides, nucleotides, nucleic acids, steroids and vitamins, when irradiated with light emitted at a wavelength preferably longer than 250 nm, especially 250 nm–780 nm, said fluorescence emission preferably being detected at wavelengths longer than 250 nm, for example 250 nm–800 nm, and using the measured values of said fluorescence emission as basis for the assessment.

Preferably, the characteristic biogenic fluorophore is NADH or NADPH, and the fluctuations in the quality of the biodegradable material is preferably assessed by on-line measurements of the fluorescence emission of one or more characteristic biogenic fluorophores.

In yet a further embodiment, the present invention relates to a waste water purification plant for biological treatment and optionally mechanical and/or chemical treatment of biodegradable material present in an aqueous environment, which plant in the biological treatment part contains at least one sensor capable of measuring the fluorescent emission and/or variations therein for at least one characteristic biogenic fluorophone present in the biological treatment part which comprises a mixed culture of microorganisms, and which plant further comprises

- a data processing means connected to the sensor, which data processing means is capable of converting the recorded fluorescent emission signal to a measurement value and comparing this measurement value to a set part, and

- a control means connected to the data processing means, which control means is adapted to control the biological and optionally mechanical and/or chemical treatment of the biodegradable material on the basis of the signal obtained from the data processing means as the result of the comparison performed therein.

Preferably, the waste water purification plant further comprises a part for determining quality and/or quantity of the biodegradable material which is to be treated in the plant, which part comprises

- a biological system comprising a mixed culture of microorganisms and a sample of the biodegradable material and at least one sensor capable of measuring the fluorescent emission and/or variations therein for at least one characteristic biogenic fluorophore present in the biological system.

- a data processing means connected to the sensor, which data processing means is capable of converting the recorded fluorescent emission signal to a measurement value and comparing this measurement value to a previous measurement value so as to evaluate fluctuations in the quantity and/or quality of the biodegradable material, and optionally,

- a control means connected to the data processing means, which control means is capable of adapting the biological and optionally mechanical and/or chemical treatment of the biodegradable material to the quantity and/or quality of the biodegradable material on the basis of the signal obtained from the data processing means as the result of the comparison performed therein.

In yet another embodiment, the present invention relates to a method of modifying or decomposing a biodegradable material present in an aqueous environment comprising subjecting the biodegradable material to at least one biological treatment and optionally one or several separation processes and/or chemical reactions in a waste water purification plant or waste decomposing plant as defined above.

Preferably, not readily biodegradable material is modified by addition of an efficient amount of a substance capable of converting or cleaving the not readily biodegradable material to material which is easily assimilable by mixed cultures of microorganisms, the substance e.g. being an enzyme such as a hydrolytic enzyme, e.g. a lipase, a protease, and/or an amylase, an oxidizing agent, an inorganic catalyst or microorganisms such as bacteria or yeast.

EXAMPLE 1

Fluorescent Emission of NADH in an Aeration Tank (Bioreactor) of a Waste Water Treatment Plant Full scale tests were carried out at The Central Purification Plant, the city of Holstebro, Denmark, a waste water treatment plant of traditional type comprising mechanical, chemical and biological treatment steps. A flow sheet is shown in FIG. 1. The plant, which originally was designed for a load of 150,000 PE, is capable of treating municipal and industrial waste water from the neighbouring community. At the time of the present experiments, the plant was treating waste water in an amount corresponding to approximately 225,000 PE.

A major part of the industrial waste water was supplied in a separate inlet (denoted "west") to the plant. This part amounted to approximately 40%, based on volume, and approximately 60%, based on BOD (Biochemical Oxygen Demand), of the total supply.

The hourly variations of the supply rate of water and of biodegradable material (in terms of BOD) were heavy. In the course of the day, the mentioned supply rates could vary as much as 6 times.

The part of the industrial waste water, which was supplied separately, was subjected to chemical precipitation by addition of hydrated lime and ferrous sulphate. By such chemical treatment, the content of biodegradable material is reduced at an early stage of the total waste water purification process so as to facilitate the later biological treatment in the aeration tanks.

The purpose of the test runs was to verify whether the NADH recording actually monitors the activity level of the mixed culture of microorganisms present in the aeration tank and whether a variation in the actual dosage of precipitation chemicals has any influence on the recording of NADH in the aeration tank. Furthermore, the effect of the actual pacing of the sensor equipment for recording the fluorescent emission of NADH in the aeration tank was investigated.

The precipitation chemicals were added directly to the waste water at a constant dosage rate prior to the primary settlement (cf. FIG. 1).

Figure 2:
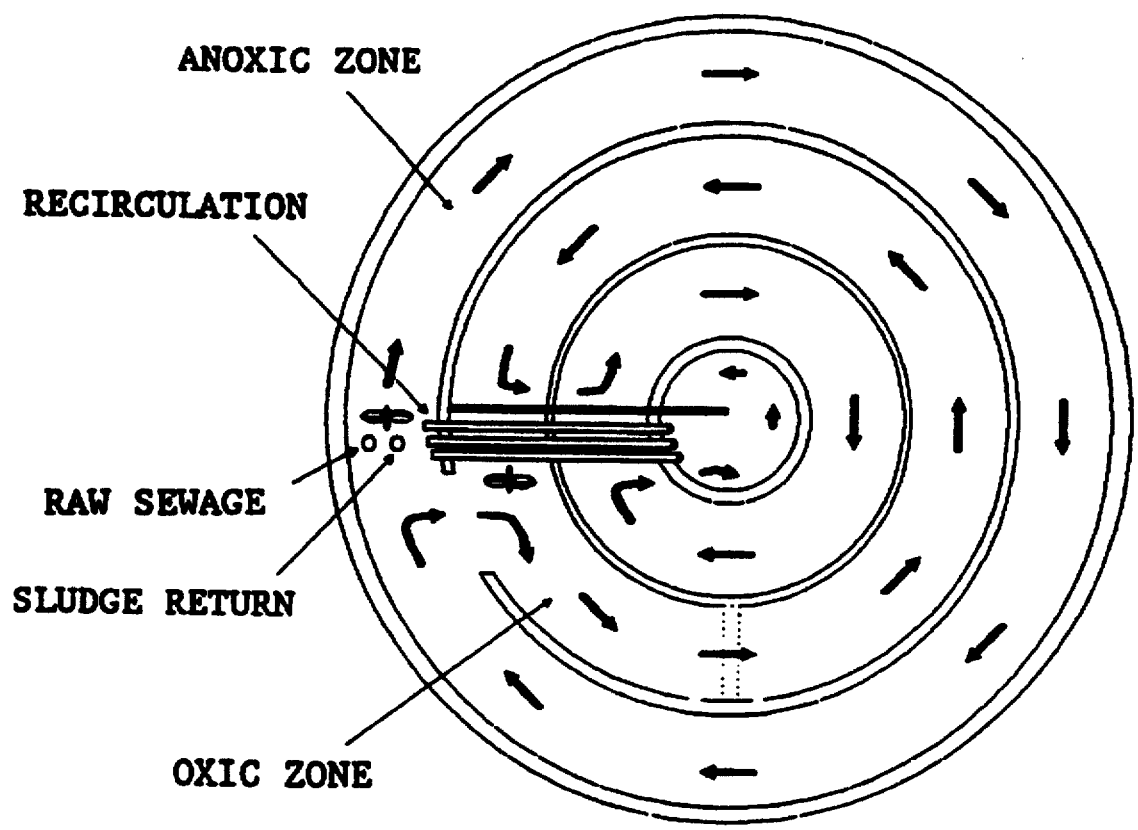
FIG. 2 shows the flow conditions of one of the aeration tanks at The Central Purification Plant, the city of Holstebro, Denmark.

In the test runs fluorescence sensor equipment (FluoroMeasure® System provided by BioChemTehnology Inc., U.S. Pat. No. 4,577,110) were used. This particular equipment is designed for laboratory use. Since the equipment was to be used outdoors, it was placed in the specially designed weatherproof box. The box was furthermore equipped with a proper heating unit so as to secure antifreeze conditions for the equipment. The box was placed in an aeration tank (cf. FIG. 1 and 2), and the level of NADH as well as the variations therein were recorded. The probe of the sensor equipment was placed in an area of the aeration tank where the incoming waste water and the activated sludge is totally mixed and the biodegradation thus is ensuing. During the test runs, the recordings have not been disturbed by any errors. In the test period, the only maintenance of the sensor equipment has been occasional cleansing operations of the probe.

Figure 3:
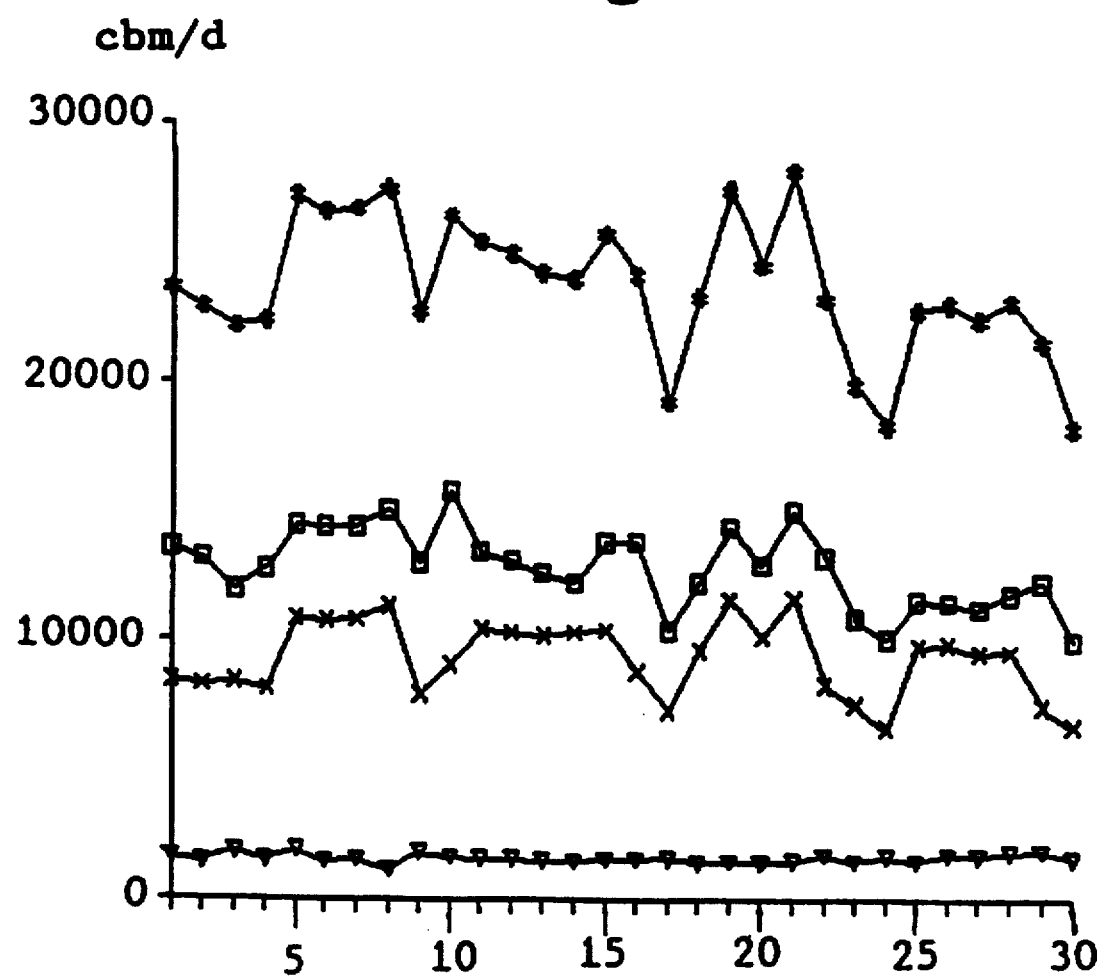
FIG. 3 shows the actual flow of incoming waste water to The Central Purification Plant, the city of Holstebro, Denmark, in the period Apr. 1st to 30th, 1988.

The operational data were the following:

| Total inlet: | app. 25,000 m³/day | (cf. FIG. 3) |
|---|---|---|
| | app. 12,000 kg/day | BOD (biodegradable material expressed as Biochemical Oxygen Demand) |
| | app. 10,000 kg/day | SS (suspended solids) |
| | app. 350 kg/day | P (phosphor) |
| | app. 1,200 kg/day | N (nitrogen) |
| Separate industrial inlet: | app. 10,000 m³/day | |

Hydrated lime (from the Applicant, Aktieselskabet Faxe Kalkbrud, Denmark) was added to the waste water prior to the flocculation at such a dosage rate a to maintain a pH of 8 (set point) in the waste water.

In the flocculation tanks, ferrous sulphate (from the Applicant, Aktieselskabet Faxe Kalkbrud, Denmark) was added to the waste water at an average dosage rate corresponding to spp. 75 kg ferrous sulphate/hr.

In the aeration tanks (bioreactors), the levels of oxygen and suspended solids, respectively, were kept constant by means of conventional equipment.

A total of 22 test runs were executed from mid-February, 1988 to the end of April, 1988. The duration of each test is shown in Table II, and during these time intervals data were recorded.

TABLE II

| Run no. | Starting date | Duration of run (hrs) | Average waste water flow (1000 cbm/d) | | | |
|---|---|---|---|---|---|---|
| | | | Day 1 | Day 2 | Day 3 | Day 4 |
| 1 | 880225 | 24 | 27.6 | | | |
| 2 | 880226 | 45 | 27.4 | 30.3 | 25.1 | |
| 3 | 880229 | 24 | 29.8 | | | |
| 4 | 880302 | 36 | 27.6 | 32.8 | | |
| 5 | 880304 | 54 | 20.2 | 23.7 | 25.0 | |
| 6 | 880307 | 36 | 27.2 | 24.3 | | |
| 7 | 880310 | 2 | 28.8 | | | |
| 8 | 880315 | 32 | 24.2 | 41.9 | | |
| 9 | 880317 | 100 | 27.7 | 26.0 | 27.1 | 24.5 |
| 10 | 880322 | 55 | 26.5 | 26.6 | | |
| 11 | 880324 | 5 | 24.1 | | | |
| 12 | 880329 | 92 | 22.0 | 30.7 | 25.7 | 23.7 |
| 13 | 880402 | 48 | 22.9 | 22.2 | | |
| 14 | 880406 | 18 | 26.7 | | | |
| 15 | 880407 | 4 | 26.7 | | | |
| 16 | 880407 | 21 | 26.7 | | | |
| 17 | 880408 | 100 | 27.5 | 22.7 | 26.5 | 25.4 |
| 18 | 880413 | 100 | 24.3 | 24.0 | 26.0 | 24.7 |
| 19 | 880418 | 79 | 23.3 | 27.5 | 24.6 | |
| 20 | 880421 | 9 | 28.2 | | | |
| 21 | 880422 | 4 | 23.3 | | | |
| 22 | 880425 | 46 | 22.7 | 23.1 | | |

In each test run, light was emitted from the fluorescence sensor equipment at a wavelength of 340 nm, and the fluorescent emission due to the presence of NADH was recorded at a wavelength of 460 nm. The fluorescent emission was recorded in terms of NFU (Normalised Fluorescence Units).

Via an interface, the sensor equipment was connected to an IBM-AX-computer including software which was capable of collecting data as well as of creating graphical presentations of these data as a function of time.

In all test runs, variations in NFU were recorded.

Based on the graphs showing the fluorescent emission of NADH as a function of time, the time of the day for recording of the maximum and minimum value, respectively, was read in order to establish a picture of the variations in the biodegradable material loading in the waste water inlet.

Test runs no. 1–6 were preliminary test runs with the purpose of a preliminary indication of the possibility for using the mentioned sensor equipment in the environment of a waste water treatment plant. These test runs turned out successfully: the equipment did record a variation in the fluorescence emission of NADH, and the daily variation was recorded to 20–35%.

In test run no. 7, the sensor equipment was placed on three different locations in the aeration tank. The variations in the recorded values were less than 10% which implies a relatively uniform recording in the aeration tank.

The purpose of test runs 8–17 and 20–22 was to gather more recordings of the fluorescence emission of NADH under normal (varying) conditions for the plant so as to be able to compare these data with other operational data from the plant. This comparison verified that the fluorescent emission recordings actually reflect the level of activity of the microorganisms which at any time are present in the aeration tank. Furthermore, the daily and weekly variations in the loading with biodegradable material were investigated as a result of the recordings: normally, the minimum values of NFU (heavy biodegradable material loading) are recorded late in the afternoon and the maximum values of NFU are recorded late at night or early in the morning (weak biodegradable material loading): and on weekdays the loading is significantly higher than during the week-ends.

Figure 4:
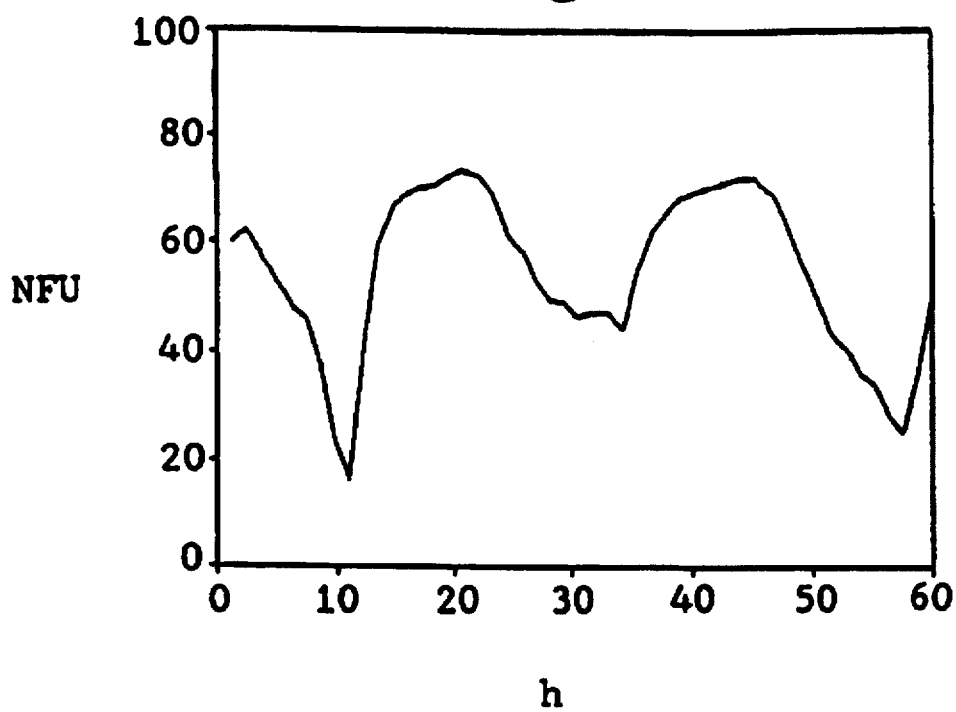
FIG. 4 shows the recorded fluorescent emission (expressed in terms of Normalised Fluorescence Units (NFU) for a period of 60 hours (corresponding to 60 hours of run No. 18 of Example 1).
Figure 5:
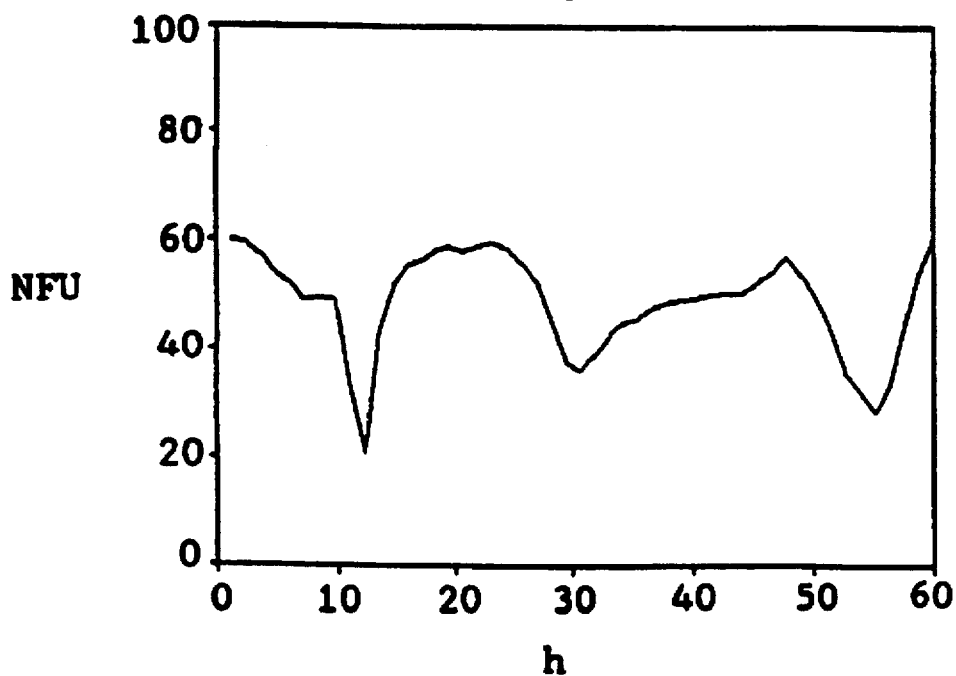
FIG. 5 shows the recorded fluorescent emission (expressed in terms of Normalised Fluorescence Units (NFU) for a period of 60 hours (corresponding to 60 hours of run No. 19 of Example 1).

In test runs no. 18 and 19, the amount of ferrous sulphate added to the waste water in the flocculation tank prior to the primary settlement was doubled from app. 75 kg ferrous sulphate/hr to app. 150 kg ferrous sulphate/hr for a period of 24 to 48 hours after each run was started. FIGS. 4 (run 18) and 5 (run 19) show the recorded fluorescent emission (in NFU) as a function of time. From the figures it is seen that the doubled amount of ferrous sulphate added to the waste water results in a much lesser decrease in NFU at the middle of the day in comparison with the preceding and the following days, respectively. The increased precipitation seems to have led to a reduction of the loading on the biological treatment step, since the recorded values of fluorescent emission of NADH in the aeration tank actually increased. This effect is very interesting since, as a result thereof, it will be possible to control the biological system and thereby get a more steady biodegradable material loading and a more efficient purification of the waste water.

From the results of all the test runs it can be seen that the daily recorded maximum value in terms of NFU is 57–90 NFU and that the daily minimum value of NFU is 15–18 NFU. It is obvious that there is a vast variation in the minimum values of NFU.

The large difference between the minimum and maximum values describes the degree of activity of the microorganisms present, and thus the difference is characterising the capacity of the biomass. The minimum values are dependent on the biodegradable material loading of the aerated biological process. Those of the minimum values which are relatively lowest have been recorded on the first days of the working week. Generally, it can be seen that these minimum values tend to increase as the week proceeds.

The recordings of the fluorescent emission of NADH are in complete accordance with the mentioned relation between NADH and the biodegradable material loading of the waste water treatment plant.

The results of the test show that it is possible to monitor the variations in the loading by on-line recording of the variations in the content of NADH in the aeration tank. Under the actual operational conditions it has been shown that the measurement of NADH has a reverse proportionality with the actual biodegradable material loading. The degree of precipitation of the incoming waste water can be estimated on the basis of such a recording of the content of NADH and the variations therein, this recording providing an on-line information bout the state of the ongoing microbiological processes.

EXAMPLE 2

Control of Biodegradable Material Loading of Biological Treatment Steps in a Waste Water Purification Plant The purpose of the experiment was to verify that it is possible to control the biodegradable material loading of the biological treatment steps in a waste water purification plant according to the method of the invention by controlling the addition of precipitation chemicals.

In November and December, 1988, full scale test runs were carried out at the same plant and basically in the same manner as the test runs of Example 1: the box with the fluorescence sensor equipment was placed in an aeration tank, and the fluorescent emission of NADH was recorded.

According to the method of the invention, the biodegradable material loading of a waste water purification plant can be monitored on-line by an on-line recording of the fluorescent emission of NADH.

Also, it is possible to decrease the biodegradable material loading (loading with biodegradable material) of the biological treatment steps, i.e. the aeration tanks, by chemical precipitation of especially the colloid particles of the biodegradable material.

Figure 6:
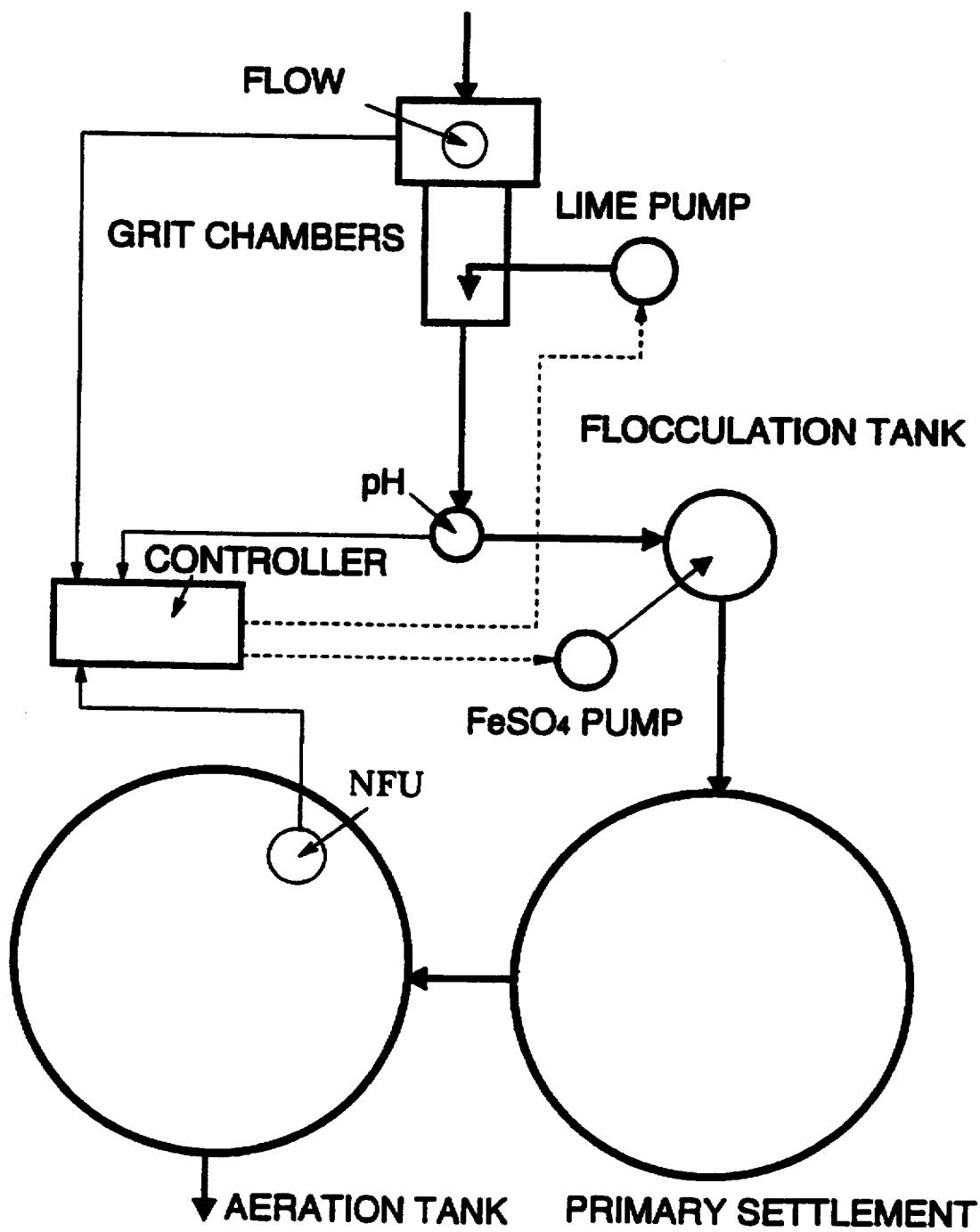
FIG. 6 shows a process control system for controlling pH by addition of hydrated lime and controlling the biodegradable material loading by addition of ferrous sulphate on the basis of the recorded values of fluorescent emission (detected at a wavelength of about 460 nm) in a biological treatment step (bioreactor).

Thus, on the basis of the above relations, precipitation chemicals were added to the waste water in the plant according to the process control diagram outlined in FIG. 6. Hydrated lime was added to the inlet waste water prior to the flocculation, and ferrous sulphate was added to the waste water in flocculation tank 1.

Operational Data

The controller was a programmable control system (SATT Control Unit (Satt Con 05-35) from Satt Control AB of Sweden).

The other equipment (apparatus for pH-measurement, flow measurement etc., pumping systems and the like) was equipment which are conventionally used in waste water purification plants.

The amount as well as the composition of the total waste water inlet and of the separate industrial waste water inlet, pH and the level of ferrous sulphate added were similar to those of Example 1.

The dosage rate of ferrous sulphate and the dosage rate of hydrated lime were controlled variables in the automatisation system of FIG. 6: the dosage rate of hydrated lime being controlled on the basis of inlet flow and pH of inlet as measured variables, and the dosage rate of ferrous sulphate being controlled on the basis of inlet flow and NADH fluorescent emission as measured variables with the set point of the latter dosage rate being determined on the basis of previous knowledge of the "usual" biodegradable material loading (cf. the results of Example 1 and of FIG. 11) of the plant, i.e. the set point is varying as a preset function of time.

Figure 9:
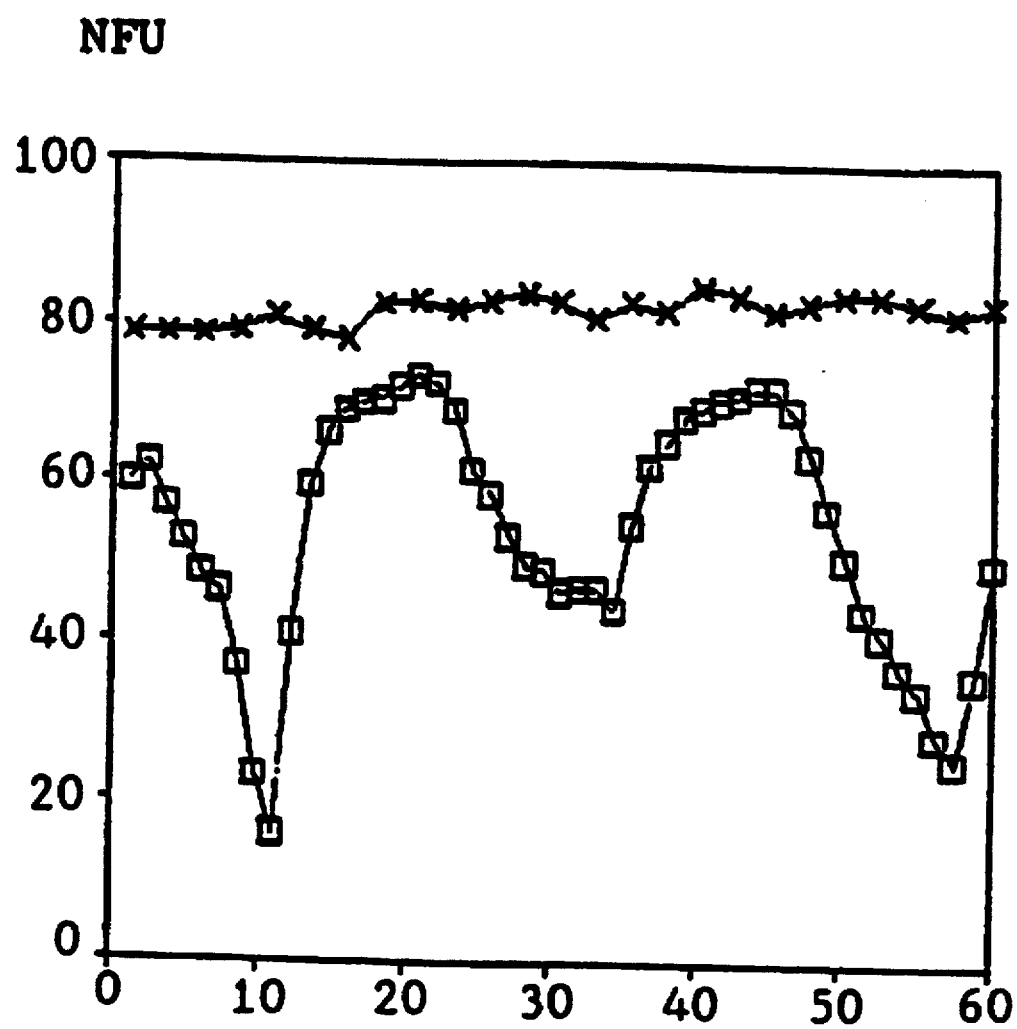
FIG. 9 shows the recorded values of fluorescent emission (in NFU, detected at a wavelength of about 460 nm) for 90 hours in each of the periods March-April, 1988 (by a conventional procedure, i.e. without controlling the biodegradable material loading of the aeration tank of The Central Purification Plant, the city of Holstebro, Denmark) and November-December, 1988 (with controlling of the biodegradable material loading of the aeration tank of The Central Purification Plant, the city of Holstebro, Denmark, in accordance with the present invention).

For comparison purposes, FIGS. 7 and 8 show the separate inlet flow of industrial waste water (cf. Example 1) to the plant for 90 hours (app. 4 days) of each of the periods March–April, 1988 and November–December, 1988, respectively. For each of the above periods, recorded values of fluorescent emission of NADH (NFU) in the aeration tank as a function of time (hours) are shown in FIG. 9. Thus, FIG. 9 shows a comparison of fluorescent emission recordings without and with controlled precipitation of biodegradable material (BOD) prior to the biological treatment. From the recordings of NADH fluorescent emission it is obvious that the method of the present invention can be used for levelling the biodegradable material loading of the biological treatment steps so as to achieve a relatively uniform loading throughout the day. However, it should be noted that FIG. 9 merely shows an approximate ideal situation; the situations "without" and "with" controlled precipitation are to be regarded as boundary situations, since it is almost impossible in practice to secure a constant inlet rate of biodegradable material.

Thus, a controlled primary settlement is most valuable for controlling the loading of the biological treatment steps (aeration tanks, bioreactors) of a waste water purification plant.

The settled material from the primary settlement tank, i.e. precipitated biodegradable material, can be used as a source for anaerobic production of biogas. A controlled primary settlement provides an increase in quantity as well as quality of the precipitated biodegradable material, and it is of great advantage for the anaerobic production of biogas that the precipitated biodegradable material is of high quality, i.e. that the biodegradable material is of such nature that the process of biological degradation of the material is longlasting as compared to other types of biodegradable material.

EXAMPLE 3

Comparison of the Actual Biodegradable Material Loading of a Waste Water Treatment Plant and the Recorded Fluorescent Emission of NADH The purpose of the experiment was to demonstrate the relation between the biodegradable material loading of a waste water treatment plant and fluorescent emission of NADH in the waste water.

The experiment was carried out at the same plant and under the same conditions as in Example 1. The fluorescent emission of NADH (in NFU) was recorded in the aeration tank. Samples of the inlet flow of waste water were analyzed for content of $BOD_5$ (Biological Oxygen Demand, 5 days), and the results of the analyses and the recordings were compared.

Figure 10:
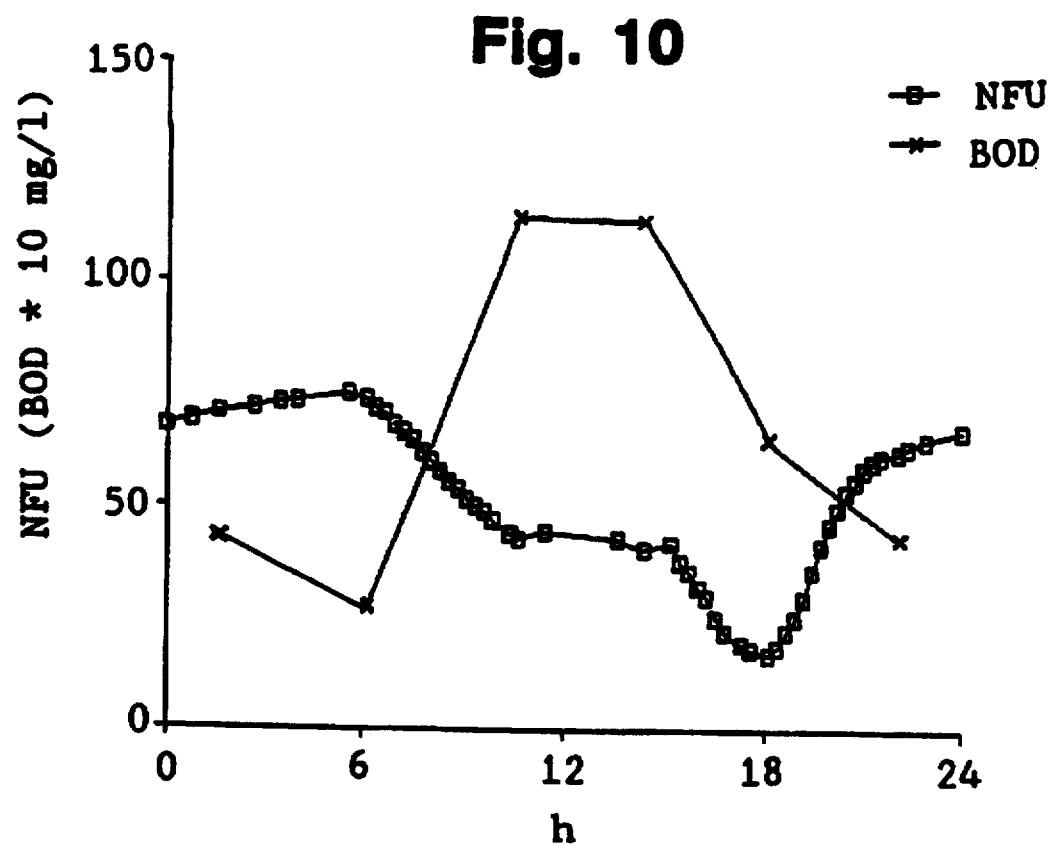
FIG. 10 shows a comparison of recorded values of fluorescent emission in the aeration tank (in NFU, detected at a wavelength of about 460 nm) and the results of the $BOD_5$ analysis of corresponding waste water samples from the aeration tank of The Central Purification Plant, the city of Holstebro, Denmark, for a period of 24 hours.

FIG. 10 shows a comparison of the results of a $BOD_5$-analysis and the corresponding fluorescent emission recordings as a function of time. An increase in the biodegradable material loading (biodegradable material) will result in a decrease of the fluorescent emission of NADH from the mixed culture of microorganisms (biomass, activated sludge) which is present in the waste water. As the biodegradable material loading decreases, the fluorescent emission level will return to the onset level.

Figure 11:
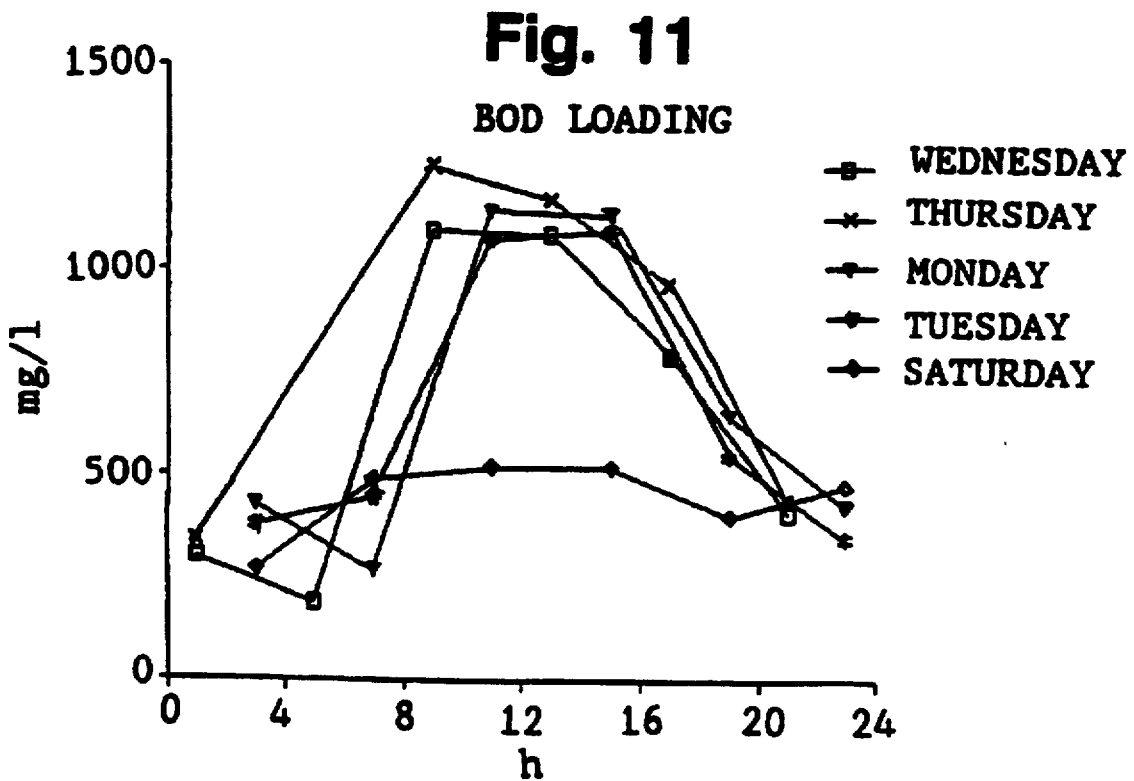
FIG. 11 shows a comparison of the daily variations in the $BOD_5$ concentration in the separate industrial waste water inlet ("west") to The Central Purification Plant, the city of Holstebro, Denmark, for a total period of 5 days in June, 1988.

The hourly variations in the biodegradable material loading is due to the industrial waste water (containing relatively high concentrations of biodegradable material) which is treated at the plant. FIG. 11 shows the results of $BOD_5$-analyses of waste water samples from the inlet. The curves illustrate the variations in the biodegradable material loading during the day for a period of 5 days. It can be seen that there are only slight variations in the biodegradable material loading during week-ends, whereas the variations during weekdays are similar to each other. Such variations in the biodegradable material loading are representative of waste water treatment plants treating municipal waste water as well as industrial waste water containing large amounts of biodegradable material.

Furthermore, it is contemplated that it is possible to monitor the biodegradable material loading of a waste water treatment plant by measurement the fluorescent emission of one or more fluorophores, for example tryptophan- and tyrosine-containing proteins, tryptophan- and tyrosine-containing peptides, tryptophan- and tyrosine-containing derivatives of amino acids, purines, pyrimidines, nucleosides, nucleotides such as NADH and NAD(P)H, nucleic acids, steroids and vitamins, in the inlet waste water to the plant, i.e. by placing the probe of the fluorescence sensor equipment in the waste water inlet stream. By monitoring the inlet waste water according to the method of the invention, it is contemplated that it is possible to gather information about the actual content of for example organic and/or biodegradable substances in the incoming waste water. Such information is most valuable and can be used as a basis for process control of the waste water treatment plant, especially for controlling the chemical reactions and/ or the biological process steps. For this purpose, it is convenient to record the fluorescence emission of more fluorophores, especially fluorophores selected from the group of fluorophores mentioned above.

EXAMPLE 4

Process control of Primary Settlement Process in a Waste Water Treatment Plant

As can be seen from the results of Example 3, it is possible to obtain on-line, quantitative information regarding the contents of biodegradable material in the inlet waste water to a waste water treatment plant by monitoring the fluorescent emission of NADH in the inlet, for example the inlet of the biological treatment steps, according to the method of the invention.

Thus, it is contemplated that it is possible to control a pretreatment of the inlet waste water, for example a chemical precipitation of especially colloid particles of biodegradable material so as to secure an optimum biodegradable material loading of the biological processes taking place in the biological treatment steps. This will result in the best possible quality of purified water in the final effluent.

For example, the control of the pretreatment can take place by controlling the chemical precipitation, i.e. the dosage rate of the precipitation chemicals added to the waste water, on the basis of on-line information of the concentration of biodegradable material of the inlet waste water.

EXAMPLE 5

Process Control of Recycled Sludge and Excess Sludge in a Waste Water Treatment Plant By using the method of the invention it is also possible to monitor the fluorescent emission of NADH in concentrated sludge. Such concentrated sludge is outlet from the aeration tanks (bioreactors of the biological treatment steps) in a waste water treatment plant comprising biological treatment steps (cf. FIG. 1). Such a monitoring gives on-line information about the level of activity of the sludge, i.e. of the microorganisms present.

Based on this monitoring, it will be possible to control the flow of recycled activated sludge and the outlet (flow) of excess sludge so as to secure that the aeration tanks (bioreactors) at any point of time include an amount of activated sludge which is convenient for an optimum biological treatment.

EXAMPLE 6

Monitoring of Outlet(s) from Waste Water Treatment Plants

The method of the invention can be used for monitoring the final effluent(s) (purified water outlet(s)) from waste water treatment plants, especially for monitoring the adequate removal of microorganisms and biodegradable material which inevitably are present in the inlet waste water to the plant. Among the microorganisms present in the inlet waste water are also pathogenic microorganisms and other microorganisms which usually indicate the presence of pathogenic microorganisms. For example, E. coli can act as an indicator for the presence of pathoenic microorganisms.

By placing the probe of fluorescence sensor equipment, for example as describe din Example 1, in the final effluent from the plant, it is possible to provide an on-line recording of fluorescent emission from one or more fluorophores such as tryptophan- and tyrosine-containing proteins, tryptophan- and tyrosine-containing peptides, tryptophan- and tyrosine-containing derivatives of amino acids, purines, pyrimidines, nucleosides, nucleotides such as NADH and NAD(P)H, nucleic acids, steroids and vitamins. Such recording is capable of providing information about the content of living microorganisms, cells, degraded cells, by-products of cell production and the like in the final effluent. It is preferred that the content of such material in the final effluent is an insignificant as possible, especially that there is no content of pathogenic microorganisms.

It is obvious that by placing the probe of fluorescence sensor equipment as described above, it is possible to gather information of the content of biodegradable material, phosphor-containing material and the like, in the final effluent. Such information could be vital for monitoring the overall efficiency of the waste water purification process.

By a monitoring as described above, the process of secondary settlement can be followed closely: it is possible to estimate whether the settlement of suspended solids and sludge (biomass) is proceeding satisfactorily. On the basis of this information, the degree of recycling of sludge from the secondary settlement as well as the inlet thereto can be controlled.

EXAMPLE 7

Monitoring of Recipients

It is contemplated that it is possible to place fluorescence sensor equipment capable of recording fluorescent emission of one or more fluorophores such as tryptophan- and tyrosine-containing proteins, tryptophan- and tyrosine-containing peptides, tryptophan- and tyrosine-containing derivatives of amino acids, purines, pyrimidines, nucleosides, nucleotides such as NADH and NAD(P)H, nucleic acids, steroids and vitamins in a measurement buoy, optionally together with other equipment capable of monitoring for example temperature, pH, salinity, concentration of oxygen and the like.

This buoy can be placed in recipients such as the sea, lakes, rivers and other waterways. Thus, it will be possible to monitor a possible microbiological activity in the waters next to the buoy, for example growth of algae.

Recording of fluorescent emission of one or more fluorophores such as tryptophan- and tyrosine-containing proteins, tryptophan- and tyrosine-containing peptides, tryptophan- and tyrosine-containing derivatives of amino acids, purines, pyrimidines, nucleosides, nucleotides such as NADH and NAD(P)H, nucleic acids, steroids and vitamins according to the method of the invention can provide information of for example cell density and growth conditions in the waters.

EXAMPLE 8

Monitoring of the Biofiltration Step in Pretreatment of Tap Water

It is often a necessity to pretreat water for use as tap water, since such water often shows microbiological activity of undesired levels.

Such treatment may for example include the following steps and/or equipment: sand catcher, cascade, sedimentation basin, infiltration basin, flocculation, sand filter, active carbon filter, injection well, percolation gallery, extraction well, aeration, design with powdered carbon, rapid filtration, secondary aeration, rinsing water collection basin, slow sand filter and sludge dewatering.

According to the method of the invention, the microbiological activity in the water can be monitored by placing fluorescence sensor equipment for example in any of the aeration steps, and thus, it is possible to collect information about the actual removal of biodegradable material in the water.

Also, according to the method of the invention, the quality of the final effluent, i.e. the potable water, can be monitored on-line by recording the fluorescent emission of one or more fluorophores such as tryptophan- and tyrosine-containing proteins, tryptophan- and tyrosine-containing peptides, tryptophan- and tyrosine-containing derivatives of amino acids, purines, pyrimidines, nucleosides, nucleotides such as NADH and NAD(P)H, nucleic acids, steroids and vitamins in the tap water outlet from the water treatment system.

EXAMPLE 9

Process Control of a Bioscrubber or a Gas Absorption Process

Bioscrubber equipment is capable of removing solid material, especially in the form of dusts or mists, from a gas by wet collection, i.e. by adding or circulating a liquid which is capable of assisting in the collection process, the liquid comprising activated sludge. Bioscrubbers can be used for purposes such as flue gas purification.

In order to monitor the level of microbiological activity according to the method of the invention, the probe of fluorescence sensor equipment can be placed in the activated sludge tank.

Gas absorption equipment provides a liquid which is capable of absorbing one or more soluble components of a gas mixture. As for bioscrubbers, gas absorption equipment can be used as an integrated part of equipment used for purposes such as flue gas purification, for example for purification of flue gasses from power stations. Such gas absorption equipment may have a design corresponding to a bioscrubber, i.e. the liquid used for gas absorption preferably contains activated sludge, the activated sludge being capable of degrading at least some of the substances in the gas mixture which are absorbed in the liquid. It is contemplated that monitoring of the level of microbiological activity according to the method of the invention can be accomplished in the same manner as described above for bioscrubbers.

Thus, it is contemplated that the level of fluorescence emission of one or more fluorophores such as tryptophan- and tyrosine-containing proteins, tryptophan- and tyrosine-containing peptides, tryptophan- and tyrosine-containing derivatives of amino acids, purines, pyrimidines, nucleosides, nucleotides such as NADH and NAD(P)H, nucleic acids, steroids and vitamins and the variations therein can be recorded so as to give on-line information which an be used as basis for controlling process parameters such as gas flow, outlet of excess sludge and degree of recycling.

EXAMPLE 10

Monitoring of the Sludge Dewatering Step in a Waste Water Treatment Plant

A waste water treatment plant comprising a biological treatment step typically includes a sludge dewatering step (cf. FIG. 1). The purpose of such a sludge dewatering step is to provide dewatered sludge with a high content of dry matter and to separate the dewatered sludge from the reject water.

According to the method of the invention, it is possible to monitor the sludge dewatering process by placing the probe of fluorescence sensor equipment in the reject water outlet. Thus, it is possible to record the fluorescence emission of one or more fluorophores such as tryptophan- and tyrosine-containing proteins, tryptophan- and tyrosine-containing peptides, tryptophan- and tyrosine-containing derivatives of amino acids, purines, pyrimidines, nucleosides, nucleotides such as NADH and NAD(P)H, nucleic acids, steroids and vitamins.

Based on such on-line recordings it can be estimated whether the sludge dewatering process is proceeding satisfactorily, i.e. at the optimum level, since increasing levels of fluorescent emission of one or more fluorophores such as tryptophan- and tyrosine-containing proteins, tryptophan- and tyrosine-containing peptides, tryptophan- and tyrosine-containing derivatives of amino acids, purines, pyrimidines, nucleosides, nucleotides such as NADH and NAD(P)H, nucleic acids, steroids and vitamins, respectively, indicate increasing amounts of proteins and microorganisms (sludge, biomass) passing through.

EXAMPLE 11

Fluorescence Emission of NADH in a Controlled Fermentation Process Response to a Glucose Pulse Injected into the Fermentation System The purpose of the experiment was to verify the theory set forth above, namely that a decrease in the relative amount of NADH indicates that the biodegradable material has a reduced biodegradability, whereas an increase in the relative amount of NADH reflects an increased biodegradability.

The conditions were the following:

| Microorganism: | yeast (DGI 342; isolate of *Saccharomyces cerevisiae*) |
|---|---|
| Fermentor: | 1 liter fermentor in a special steel tank including stirrer, pH control device, oxygen measurement device (Ingold), temperature measurement device (PR2202 with Pt100 sensor) and an externally controlled pump |
| Substrate: | standard according to Egli, based on 1% w/w glucose as limiting substrate (10 g/l glucose). |
| Fermentation: | temperature: 25° C. |
| | pH: 4 |
| | D: 0.1 hr$^{-1}$ (rate of dilution) |
| | volume: 700 ml |
| Analyses: | OD |
| | CTS |
| | Glucose (Yellow Springs Analyzer) |

A chemostat is operated according to the above conditions. The substrate which is continuously fed into the fermentor has a concentration implying starvation of the microorganisms. After an operation period of 48 hours, a pulse of 1.4 g glucose is injected into the fermentor.

Figure 12:
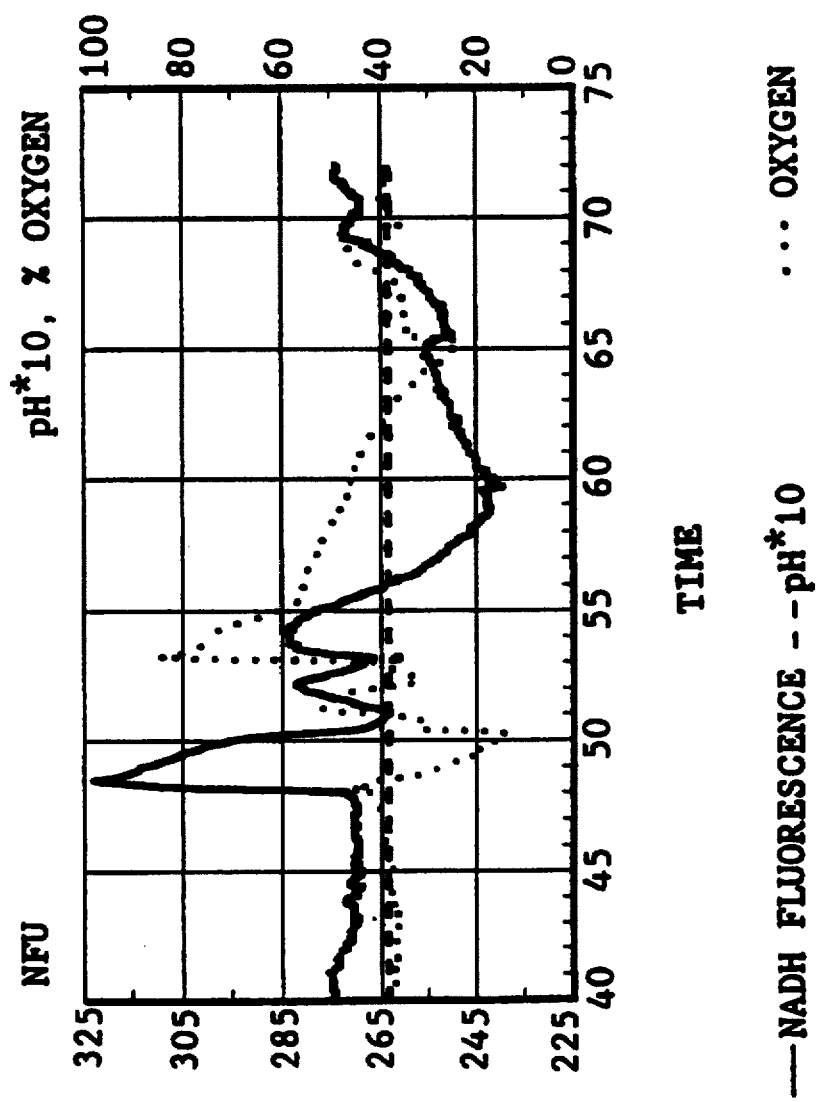
FIG. 12 shows the results of measurements of NADH fluorescence, oxygen content and pH in a controlled fermentation process, wherein a sudden glucose pulse is imposed, cf. example 11 below.

FIG. 12 shows the corresponding measurements of NFU, pH and content of oxygen (in per cent) in the fermentor in the period +40 hrs. to +75 hrs.

From the figure it is appreciated that the recording the NFU increases momentaneously upon the glucose injection from app. 270 NFU to app. 320 NFU. This result emphasizes the effect of addition of readily biodegradable carbon sources (in this case glucose is used) on the NADH fluorescence measurement: a marked increase in the recorded NFU value. From the maximum value (the peak), the recorded NFU signal decreases over a period of app. 3 hours, and simultaneously a decrease in the oxygen content takes place; this is due to transfer of the energy available as NADH to other forms of energy that are more suitable under the prevailing conditions.

The smaller peaks (recorded NFU) occurring at 52 and 54 hrs. respectively, can be attributed to degradation products and are described in the literature.

I claim:

1. A waste water purification plant operable for biological treatment and optionally for mechanical and/or chemical treatment of biodegradable material present in an aqueous environment, which plant in a biological treatment part contains at least one first sensor which is operable for measuring fluorescent emission and/or variations therein of at least one characteristic biogenic fluorophore present in the biological treatment part which comprises a first mixed culture of microorganisms, and which plant further comprises:

a first data processing means connected to the at least one first sensor, which first data processing means is operable for converting a recording fluorescent emission signal to a measurement value and comparing said measurement value to a predetermined set point which indicates optimum or near optimum conditions for the first mixed culture of microorganisms with respect to the biodegradation of the biodegradable material.

a first control means connected to the first data processing means, which first control means is adapted to control the biological and optionally mechanical and/or chemical treatment of the biodegradable material on the basis of the signal obtained from the first data processing means as the result of the comparison performed therein, so as to move subsequent fluorescence measurements toward the pre-determined set point, whereby conditions in the biological treatment part are adapted in the direction of optimum or near optimum conditions for the first mixed culture of microorganisms with respect to biodegradation of the biodegradable material, said at least one characteristic biogenic fluorophore being one which is present in the first mixed culture of microorganisms and acts as indicator of the metabolic activity of the first mixed culture of microorganisms; and a portion for determining quality and/or quantity of the biodegradable material which is to be treated in the plant, which portion comprises a biological system comprising a second mixed culture of microorganisms and a sample of the biodegradable material and at least one second sensor which is operable for measuring fluorescent emission and/or variations therein of at least one characteristic biogenic fluorophore present in the biological system.

2. A waste water purification plant according to claim 2, wherein the at least one characteristic biogenic fluorophore measured by the at least one first sensor each is selected from the group consisting of tryptophan- and tyrosine-containing proteins, tryptophan- and tyrosine-containing peptides, tryptophan- and tyrosine-containing derivatives of amino acids, purines, pyrimidines, nucleosides, nucleotides, nucleic acids, steroids and vitamins and mixtures thereof.

3. A waste water purification plant according to claim 2, wherein the at least one characteristic biogenic fluorophore measured by the at least one first sensor each is a nicotin-amide adenine dinucleotide selected from the group consisting of NADH and NAPH and mixture thereof.

4. A waste water purification plant according to claim 1, wherein the portion for determining quality and/or quantity of the biodegradable material which is to be treated in the plant further comprises:

a second data processing means connected to the at least one second sensor, which second data processing means is operable for converting a measured fluorescent emission signal to a measurement value and compares measurement value to a previous measurement value so as to evaluate fluctuations in the quantity and/or quality of the biodegradable material, and optionally, a second control means connected to the second data processing means, which second control means is capable of adapting a subsequent biological and optionally mechanical and/or chemical treatment of the biodegradable material to the quantity and/or quality of the biodegradable material on the basis of the signal obtained from the second data processing means as the result of the comparison performed therein.

5. A waste water purification plant according to claim 4, wherein the at least one characteristic biogenic fluorophore measured by the at least one second sensor each is selected from the group consisting of tryptophan- and tyrosine-containing proteins, tryptophan- and tyrosine-containing peptides, tryptophan- and tyrosine-containing derivatives of amino acids, purines, pyrimidines, nucleosides, nucleotides, nucleic acids, steroids and vitamins and mixtures thereof.

6. A waste water purification plant according to claim 5, wherein the at least one characteristic biogenic fluorophore measured by the at least one second sensor each is a nicotin-amide adenine dinucleotide selected from the group consisting of NADH and NAPH and mixtures thereof.

* * * * *

UNITED STATES PATENT AND TRADEMARK OFFICE
CERTIFICATE OF CORRECTION

PATENT NO. : 5,700,370

DATED : DECEMBER 23, 1997

INVENTOR(S) : HELMO

It is certified that error appears in the above-identified patent and that said Letters Patent is hereby corrected as shown below:

In column 1, line 6: "5,500,906" should read —5,506,096—.

In column 1, line 25: "lift" should read —life—.

In column 1, line 43: "not" should read —now—.

In column 4, line 46: Insert —of— after "method".

In column 6, line 42: "wise" should read —wide—.

In column 6, line 48: "(Paramecium)" should read —(Paramaecium)—.

In column 8, line 39: "or" should read —of—.

In column 10, line 57: "biological" should read —Biological—.

In column 11, line 35: "seen" should read —seem—.

In column 12, line 50: "materials" should read —material—.

In column 13, line 8: "assimible" should read —assimilable—.

In column 14, line 22: "fluorophors" should read —fluorophore—.

UNITED STATES PATENT AND TRADEMARK OFFICE
CERTIFICATE OF CORRECTION

PATENT NO. : 5,700,370

DATED : DECEMBER 23, 1997

INVENTOR(S) : HELMO

It is certified that error appears in the above-identified patent and that said Letters Patent is hereby corrected as shown below:

In column 14, line 25: "tryptophen" should read —tryptophan—.

In column 14, line 52: "assimilible" should read —assimilable—.

In column 15, line 23: "assimilible" should read —assimilable—.

In column 16, lines 15 and 17: "quarts" should read —quartz—.

In column 17, line 28: "seration" should read —aeration—.

In column 19, line 44: "pacing" should read —placing—.

In column 20, line 19: "spp" should read —app—.

In Table II, for Run No. 5: "20.2" should read —30.2—.

In Table II, for Run No. 11: "24.1" should read —34.1—.

In Table II, for Run No. 12: "22.0" should read —32.0—.

In column 22, line 8: "bout" should read —about—.

In column 25, line 14: "pathoenic" should read —pathogenic—.

In column 25, line 16: "din" should read —in—.

In column 27, line 5: "an" should read —can—.

UNITED STATES PATENT AND TRADEMARK OFFICE
CERTIFICATE OF CORRECTION

PATENT NO. : 5,700,370  PAGE 3 of 3
DATED      : DECEMBER 23, 1997
INVENTOR(S): HELMO

It is certified that error appears in the above-identified patent and that said Letters Patent is hereby corrected as shown below:

In claim 1 (column 28, at line 35):   "recording" should read —recorded—.

In claim 2 (column 29, at line 1):    "2" should read —1—.

In claim 3 (column 29, at line 13):   "NAPH" should read —NADPH—.

In claim 3 (column 29, at line 13):   "mixture" should read —mixtures—.

In claim 4 (column 29, at line 21):   Insert —second— after "a".

In claim 4 (column 29, at line 22):   Insert —said second— after "compares".

In claim 6 (column 30, at line 23):   "NAPH" should read —NADPH—.

Signed and Sealed this

Ninth Day of February, 1999

Attest:

Attesting Officer

*Acting Commissioner of Patents and Trademarks*